US009435900B2

(12) United States Patent
Yao et al.

(10) Patent No.: US 9,435,900 B2
(45) Date of Patent: Sep. 6, 2016

(54) X-RAY SYSTEM UTILIZING ALTERNATING SPECTRUM X-RAY SOURCE IN CONJUCTION WITH A FIXED SPECTRUM SEPARATION FILTER APPROVAL

(75) Inventors: Yuan Yao, Stanford, CA (US); Norbert J. Pelc, Los Altos, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 514 days.

(21) Appl. No.: 13/491,412

(22) Filed: Jun. 7, 2012

(65) Prior Publication Data
US 2012/0314834 A1 Dec. 13, 2012

Related U.S. Application Data

(60) Provisional application No. 61/494,809, filed on Jun. 8, 2011.

(51) Int. Cl.
| | | |
|---|---|---|
| G01N 23/087 | (2006.01) | |
| A61B 6/00 | (2006.01) | |
| G01T 1/29 | (2006.01) | |
| G01N 23/04 | (2006.01) | |

(52) U.S. Cl.
CPC ........... *G01T 1/2985* (2013.01); *A61B 6/4042* (2013.01); *G01N 23/046* (2013.01); *G01N 23/087* (2013.01); *G01N 2223/419* (2013.01)

(58) Field of Classification Search
CPC .......................... G01T 1/2985; G01N 23/046
USPC ...................................................... 378/5, 62
See application file for complete search history.

(56) References Cited

U.S. PATENT DOCUMENTS

| | | | | |
|---|---|---|---|---|
| 4,288,695 A | * | 9/1981 | Walters .................. | A61B 6/032 378/159 |
| 5,115,394 A | * | 5/1992 | Walters ........................ | 382/131 |
| 5,396,530 A | * | 3/1995 | Tsutsui .................. | G06T 11/005 348/E5.089 |
| 5,485,492 A | * | 1/1996 | Pelc ....................... | A61B 6/032 378/4 |
| 5,570,403 A | * | 10/1996 | Yamazaki et al. ................ | 378/5 |
| 5,661,774 A | * | 8/1997 | Gordon et al. ............... | 378/101 |
| 6,115,452 A | * | 9/2000 | Marrs .................... | A61B 6/481 378/119 |
| 6,904,118 B2 | * | 6/2005 | Wu et al. .......................... | 378/5 |
| 7,826,587 B1 | | 11/2010 | Langan et al. | |
| 2005/0053189 A1 | * | 3/2005 | Gohno et al. .................. | 378/16 |
| 2007/0041490 A1 | * | 2/2007 | Jha et al. ......................... | 378/8 |
| 2009/0168949 A1 | * | 7/2009 | Bendahan et al. ............... | 378/5 |
| 2010/0008558 A1 | * | 1/2010 | Baeumer et al. ............ | 382/131 |
| 2010/0014737 A1 | * | 1/2010 | Ruhrnschopf et al. ....... | 382/131 |

OTHER PUBLICATIONS

Primak et al., "Improved dual-energy material discrimination for dual-source CT by means of additional spectral filtration," Medical Physics, vol. 36, issue 4, Apr. 2009, pp. 1359-1369.
Siewerdsen et al., "Spektr: A computational tool for x-ray spectral analysis and imaging system optimization," Medical Physics, vol. 31, issue 11, Nov. 2009, pp. 3057-3067.

* cited by examiner

*Primary Examiner* — Nicole Ippolito
*Assistant Examiner* — Sean Luck
(74) *Attorney, Agent, or Firm* — Beyer Law Group LLP

(57) ABSTRACT

An apparatus for x-ray imaging of an object is provided. An x-ray source for providing alternating x-ray spectrums is placed on a first side of the object. A spectrum separation fixed filter is placed between the x-ray source and the object. An x-ray detector is placed on a second side of the object opposite the x-ray source. A controller controls the x-ray source and the x-ray detector.

19 Claims, 30 Drawing Sheets

X-RAY SYSTEM UTILIZING ALTERNATING SPECTRUM X-RAY SOURCE IN CONJUCTION WITH A FIXED SPECTRUM SEPARATION FILTER APPROVAL

CROSS REFERENCE TO RELATED APPLICATIONS

This application claims priority under 35 U.S.C. §119(e) from U.S. Provisional Patent Application No. 61/494,809, filed on Jun. 8, 2011, entitled "Efficacy of Fixed Filtration for Rapid KVP-Switching Dual Energy X-Ray Systems" which is hereby incorporated by reference for all purposes.

BACKGROUND OF THE INVENTION

This invention relates generally to x-ray imaging processes and systems that use two or more x-ray spectra.

Conventional x-ray imaging uses a single kVp during a scan and represents an observed object in terms of its attenuation. However, this information is not sufficient to precisely characterize the observed object, since attenuation is energy dependent. In the diagnostic energy range, x-ray attenuation is the combination of two photon-matter interactions: the photoelectric effect and Compton scattering. These two interactions are energy-dependent and reflect the effective atomic number and electron density of the object. Accordingly, two measurements at distinct energy spectra can separate the attenuation information into these two basic components, which allows for better identification of the materials present in the object, contrast material specific images, or a weighted sum of the two interactions.

Larger spectral separation of the low and high energy spectra is favorable to image variance deduction, therefore it contributes to reducing the total radiation dose of each scan while maintaining the same noise level of the output image.

SUMMARY OF THE INVENTION

In accordance with the invention, an apparatus for x-ray imaging of an object is provided. An x-ray source for providing alternating x-ray spectra (or spectrums) is placed on a first side of the object. A spectrum separation fixed filter is placed between the x-ray source and the object. An x-ray detector is placed on a second side of the object opposite the x-ray source. A controller controls the x-ray source and the x-ray detector.

In another manifestation of the invention, a method for providing x-ray imaging of an object is provided. An x-ray source is provided with at least two different alternating kVp values with a first kVp potential and a second kVp potential. The alternating kVp x-rays are passed through a spectrum separation fixed filter, wherein the spectrum separation fixed filter increases spectrum separation between x-rays with the first kVp potential and x-rays with the second kVp potential. The x-rays are passed through the object. The x-rays that pass through the object at the first kVp potential and the second kVp potential are detected at a detector. Material decomposition is applied to detected x-rays. The material decomposition is used to generate an image.

The invention and objects and features thereof will be more readily apparent from the following detailed description and appended claims when taken with the drawings.

DETAILED DESCRIPTION OF ILLUSTRATED EMBODIMENTS

Figure 1:
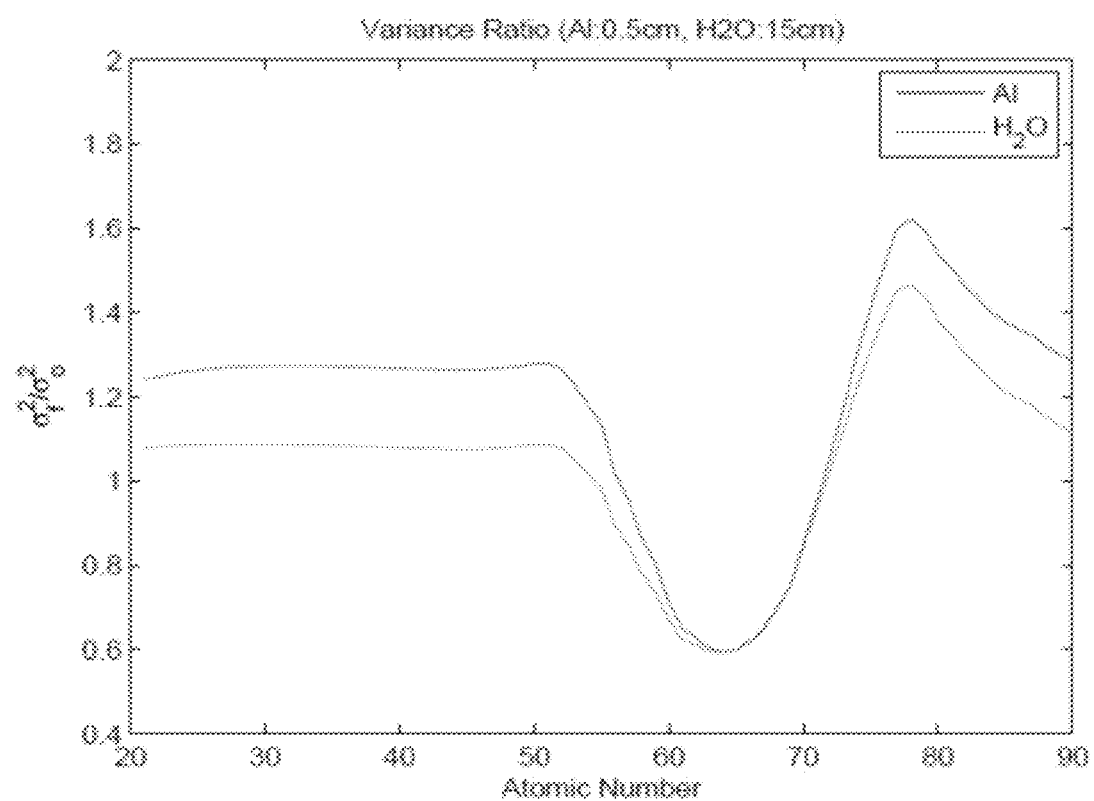
FIG. 1A shows the variance ratio of each material decomposition with filtration over without filtration against different atomic numbers.
FIG. 1B shows the same decomposition variance ratio for atomic numbers varying from 55 to 71, where that variance ratio with and without filtration is less than one.
Figure 1:
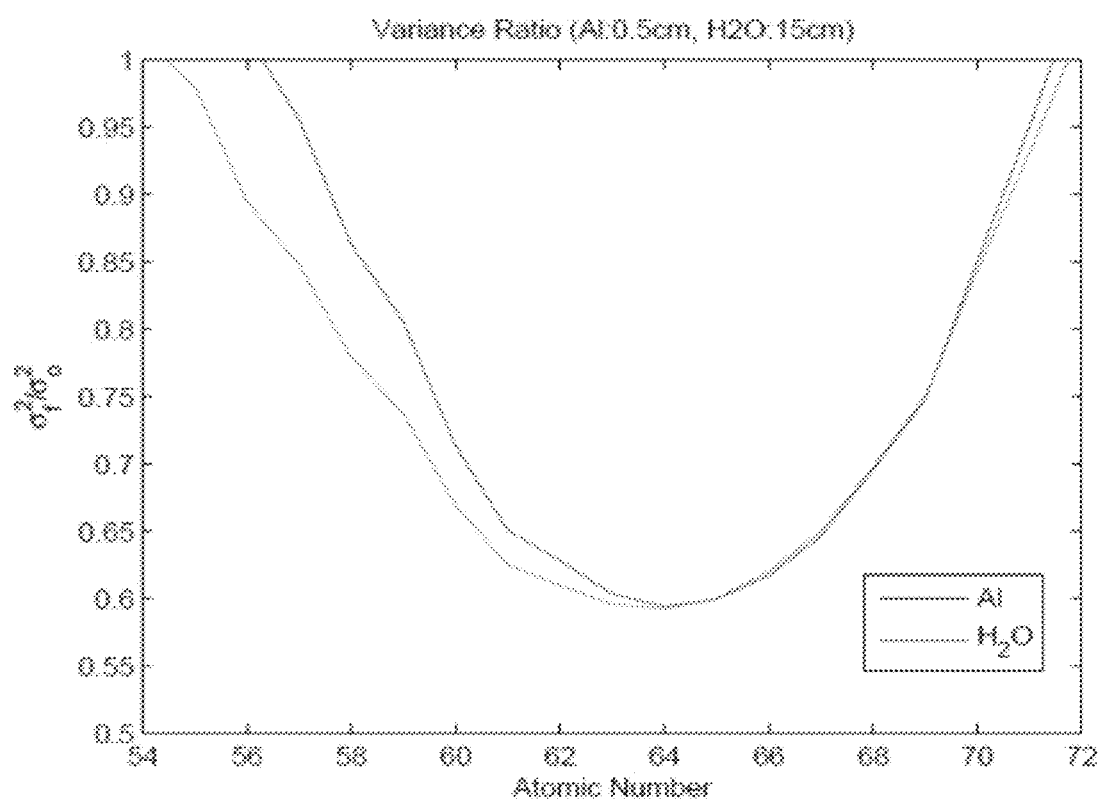

Dual energy x-ray imaging, including dual energy radiography (DER) and dual energy computed tomography (DECT), utilizes two effective spectra to obtain a low and high energy scan. There are a number of implementations of dual energy imaging, including dual sources, dual layer detectors, and rapid peak kilovolt (kVp) switching. The decomposition of an object into its representative components can be done with the raw data or the reconstructed images. An embodiment of the invention comprises a rapid kVp switching system with material decomposition coming from the raw data. This system acquires a low and high energy projection by rapidly switching the kVp of the x-ray tube. Because the two measurements are performed in rapid succession, motion is negligible and material decomposition can be performed with the raw data. Furthermore, using raw data has the advantage of providing a decomposition that is free of beam hardening effects.

The material decomposition performance of a system depends on several factors—one important factor is the energy separation between the low and high energy spectra. Because spectra from x-ray tubes are polychromatic and have significant overlap, dual energy x-ray systems can use two separate pre-patient filters to increase the energy separation between the spectra. Work has been done to optimize the filter selection for both DER and DECT, including specific, task-based applications to chest radiography and mammography. Primak et al in A. N. Primak, J. C. Ramirez Giraldo, X. Liu, L. Yu and C. H. McCollough, Med Phys 36 (4), 1359-1369 (2009) have shown that a tin filter applied to only the high energy spectrum increases the energy separation and improves the DECT performance across a range of imaging tasks.

While it has been shown that separate filters on the low and high energy spectra can be beneficial, this may be difficult to implement for rapid kVp-switching systems due to the precise synchronization of filtration exchange and x-ray tube firing needed. Therefore, an embodiment of the invention uses a spectrum separation fixed filter applied to both spectra to improve the material decomposition precision performance. An embodiment of the invention provides an optimized spectrum separation fixed filter with improved the dose efficiency of dual energy x-ray imaging with little or no impact on complexity and cost.

In the following Simulation section, DER scanning and the material decomposition of water-aluminum phantom under the clinical kVp settings was simulated, and through each possible K-edge filter's performance on variance reduction was looked at. Metallic Gadolinium was found to be an optimal filter material due to its better performance and easy availability. To lower the experimental cost, Gadolinium oxysulfide, a common x-ray phosphor component, was selected as a testing filter. Then in the Materials Section, the K-edge filter on a benchtop system was tested. Although the kVp settings were not the same as what is used clinically (due to system limitations), the embodiment was able to show that the fixed K-edge filter still provided improvement to the material decomposition precision. This was confirmed in simulations of the benchtop setup.

Simulation of K-Edge Filters

The initial search for an optimized spectrum separation fixed filter was done in simulation. Spektr, as described by J. H. Siewerdsen, A. M. Waese, D. J. Moseley, S. Richard and D. A. Jaffray, in "Spektr: A computational tool for x-ray spectral analysis and imaging system optimization," Med Phys 31 (11), 3057-3067 (2004), was used to generate discrete, x-ray spectra at 80 and 140 kVp, which reflect the low and high kVp used in clinical DECT scanners. The transmission of these spectra was simulated through a range of mixtures of aluminum and water, a commonly used material-pair in dual energy phantom studies. Note, however, that the pair of materials selected can be converted into any other pair of materials as long as they do not contain K-edges. The mean detected intensity for an energy integrating detector is given as:

$$\bar{I}_i = \int E \cdot \bar{I}_{0,i}(E) e^{-\mu_{M_1}(E) t_{M_1} - \mu_{M_2}(E) t_{M_2}} \cdot D(E) dE \quad (1)$$

where i is either low (l) or high (h) energy; $M_1$, $M_2$ refer to the two materials, aluminum (Al) and water ($H_2O$) in this case, which have thicknesses and attenuation coefficients denoted as $t_{M_1}$, $t_{M_2}$ and $\mu_{M1}(E)$, $\mu_{M2}(E)$ respectively; D(E) is the detector absorption efficiency. The attenuation coefficients were obtained from J. H. a. S. Hubbell, S. M., (National Institute of Standards and Technology (NIST), Gaithersburg, Md., 2004.

Given the discrete x-ray spectra, the integration above can be approximated as the summation:

$$\bar{I}_i = \sum_E E \cdot \bar{I}_{0,i}(E) e^{-\mu_{M_1}(E) t_{M_1} - \mu_{M_2}(E) t_{M_2}} \cdot D(E) \quad (2)$$

In practice, there will be both quantum and electronic noise involved during data acquisition. We will assume that we operate in a regime where quantum noise is dominant, so we will ignore electronic noise in our simulation. Poisson statistics were applied so that the number of detected photons at each energy Φ(E) follows a Poisson distribution and the detected signal $I_i$ is a random variable.

$$\Phi(E) \sim \text{Poisson}(\bar{I}_{0,i}(E) e^{-\mu_{M_1}(E) t_{M_1} - \mu_{M_2}(E) t_{M_2}} \cdot D(E)) I_i = \sum_E E \cdot \Phi(E) \quad (3)$$

To solve the inverse problem of material decomposition—identifying the thicknesses based on the detected signal intensities—we applied a third order polynomial fit to map the log-normalized intensities $L_l$, $L_h$ to the known aluminum and water thicknesses, i.e.

$$L_i = \ln\left(\frac{\sum_E E \cdot I_{0,i}(E) \cdot D(E)}{I_i}\right) \quad (4)$$

$$\hat{t}_M = b_{M,1} L_l^3 + b_{M,2} L_l^2 L_h^2 + b_{M,3} L_l L_h^3 + b_{M,4} L_h^3 + b_{M,5} L_l^2 + b_{M,6} L_l L_h + b_{M,7} L_h^2 + b_{M,8} L_l + b_{M,9} L_h \quad (5)$$

where the decomposed material thickness is $\hat{t}$, M denotes the decomposition material, and $L_l$, $L_h$ are the log-normalized low and high energy measurements, respectively. The coefficients $b_{M,j}$ are calculated from measurements of a set of objects with known thicknesses. We first simulated water-aluminum pairs of different thickness with the thickness of water ranging from 0.4 to 20 cm with step size 0.4 cm and the thickness of aluminum ranging from 0.02 to 1 cm with step size 0.02 cm. Given the known phantom thicknesses, intensity measurements were simulated based on Eqs. (2). Finally, we found coefficients $b_{M,j}$ by fitting the log-normalized intensities to the known thicknesses through least square regression. The third-order polynomial was selected because we found empirically that it balanced the computational load and speed with reasonable accuracy. We forced the constant term of this polynomial equation to be zero to ensure that when there is no attenuation of the beam, the estimated decomposition is zero.

Because the detected intensities are themselves noisy, the estimated material thicknesses $\hat{t}$ will be as well. Therefore, the choice of low and high energy spectra, which determine the noise in the detected intensities, will determine the noise in the decomposition. In particular, we examined the noise (i.e., precision) in the decomposition of an object that can be represented by 0.5 cm of Al and 15 cm of water. The precision was calculated using the propagation of uncertainty, which maps quantum noise to noise in material decomposition, as described in the next paragraph.

Instead of Monte Carlo simulation, propagation of uncertainty was used to evaluate the variance of the decomposition. It was assumed that Poisson noise was the dominant noise source in the intensity measurements. According to the theory of error propagation, the precision of the decomposition can be approximated by $$\sigma^2(\hat{t}_M) = \left(\frac{\partial \hat{t}_M}{\partial I_l}\right)^2 \sigma^2(I_l) + \left(\frac{\partial \hat{t}_M}{\partial I_h}\right)^2 \sigma^2(I_h) \tag{6}$$

$$\sigma^2(I_i) = \sum_E E^2 \cdot I_{0,i}(E) e^{-\mu_{M_1}(E)t_{M_1} - \mu_{M_2}(E)t_{M_2}} \cdot D(E) \tag{7}$$

where $\hat{t}_M$ is the polynomial fit function, M denotes the decomposition material, and $I_l$, $I_h$ are the detected intensities that are independent of each other. To reduce the simulation time, we numerically calculated the Jacobian matrix instead of finding a polynomial fit every time the incident spectra changed. To be more specific, the expected intensities were calculated when an incremental change (0.01% increment or decrement) was made to a material thickness, denoted as + and −, allowing for the partial derivative of $I_i$ with respect to $\hat{t}_M$ to be calculated numerically. The Jacobian of the decomposition is the matrix inverse of the Jacobian of the measured intensities with respect to object size and allows us to find the partial derivative of estimated thickness with respect to detected intensity, as will be used in Eq. (10).

$$J \approx \begin{bmatrix} \frac{I_l^+ - I_l^-}{t_{M_1}^+ - t_{M_1}^-} & \frac{I_h^+ - I_h^-}{t_{M_1}^+ - t_{M_1}^-} \\ \frac{I_l^+ - I_l^-}{t_{M_2}^+ - t_{M_2}^-} & \frac{I_h^+ - I_h^-}{t_{M_2}^+ - t_{M_2}^-} \end{bmatrix} \Longrightarrow J^{-1} = \begin{bmatrix} \frac{\partial \hat{t}_{M_1}}{\partial I_l} & \frac{\partial \hat{t}_{M_1}}{\partial I_h} \\ \frac{\partial \hat{t}_{M_2}}{\partial I_l} & \frac{\partial \hat{t}_{M_2}}{\partial I_h} \end{bmatrix}$$

We hypothesized that a K-edge filter would provide the energy selectivity needed to remove overlap of the spectra and hence increase the precision. Possible K-edge filters were tested by exhaustively searching over all atomic numbers across the periodic table. Another parameter we optimized was the mAs allocation ratio between the low and high energy spectra ($mAs_{Low(80\ kVp)} / mAs_{High(140\ kVp)}$). While we found that thicker filters yield greater precision improvement, in this section the thickness of the filter was subject to no more than a 50% loss of intensity due to filtration. The total energy incident on the object with filtration was maintained to be the same (same total incident energy, STIE) as without filtration by scaling the filtered low and high energy spectra up by an adequate amount while keeping the mAs ratio of low to high unchanged. The detector absorption efficiency was that of a 600 μm CsI scintillator.

Finally, both the average energy $E_{avg,i}$ for an energy integrating detector and the effective energy $E_{eff,i}$ of the detected spectra were calculated to demonstrate the increasing spectral separation due to the filter. The effective energy is the photon energy corresponding to the effective attenuation coefficient. More specifically, since the attenuation coefficient is a function of energy, we can find the effective energy if the effective attenuation coefficient is known.

$$E_{avg,i} = \frac{\sum_E E^2 \cdot I_{0,i}(E) e^{-\mu_{M_1}(E)t_{M_1} - \mu_{M_2}(E)t_{M_2}} \cdot D(E)}{\sum_E E \cdot I_{0,i}(E) e^{-\mu_{M_1}(E)t_{M_1} - \mu_{M_2}(E)t_{M_2}} \cdot D(E)} \tag{8}$$

$$E_{eff,i} = \mu_M^{-1}(\mu_{eff,M}) \tag{9}$$

where $\mu_{eff,M}^{-1}(E)$ is the inverse function of the attenuation coefficient, the material M is commonly used as aluminum. Given the discrete polychromatic spectra used in the simulation, the effective attenuation coefficient is given as $$\mu_{eff,M} = \frac{dL_i}{dt_{eff,M}} = \frac{\sum_E \mu_M E \cdot I_{0,i}(E) e^{-\mu_{M_1}(E)t_{M_1} - \mu_{M_2}(E)t_{M_2}} \cdot D(E)}{\sum_E E \cdot I_{0,i}(E) e^{-\mu_{M_1}(E)t_{M_1} - \mu_{M_2}(E)t_{M_2}} \cdot D(E)} \tag{10}$$

Initial K-Edge Filter Simulation Results

To find the optimal filter material, we did an exhaustive search throughout the element table. FIG. 1A shows the variance ratio of each material decomposition with filtration over without filtration against different atomic numbers, where $\sigma_f^2$ denotes the variance with filtration and $\sigma_u^2$ refers to the variance of the original, unfiltered case, where the atomic number varies from 20 to 90. The variance reduction of almost 40% demonstrates that improved precision at a fixed dose (or lower dose for the same precision) can be achieved with optimal filtration. FIG. 1B shows the same decomposition variance ratio for atomic numbers varying from 55 to 71, where that variance ratio with and without filtration is less than one. For the object used in FIGS. 1A-B (0.5 cm Al, 15 cm water), the optimal filter material was Gadolinium (Z=64). The curve at optimal range, however, is flat, which reflects the flexibility of filter material choices. The optimal filter material does depend on the object composition and ranges from Z=55 to 71 (the lanthanide series, approximately) for different objects. Generally, the variance ratio of the water decomposition is lower than that of aluminum, which indicates that the water estimate will benefit more from this K-edge filtration since we want smaller variance. The variance ratio depends on the materials used as basis functions for the decomposition.

Figure 2:
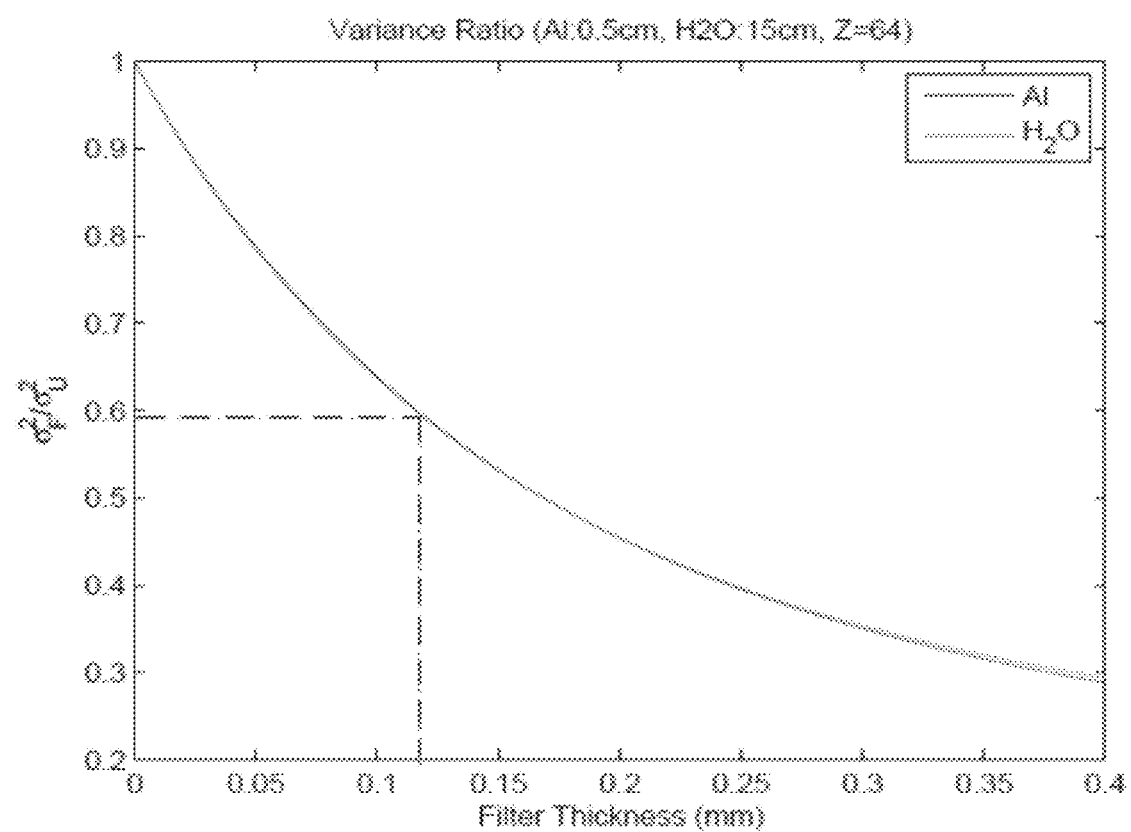
FIG. 2A is a graph of the decomposition variance ratio as a function of filter thickness.
FIG. 2B is a graph of transmitted dose as a function of filter thickness.
Figure 2:
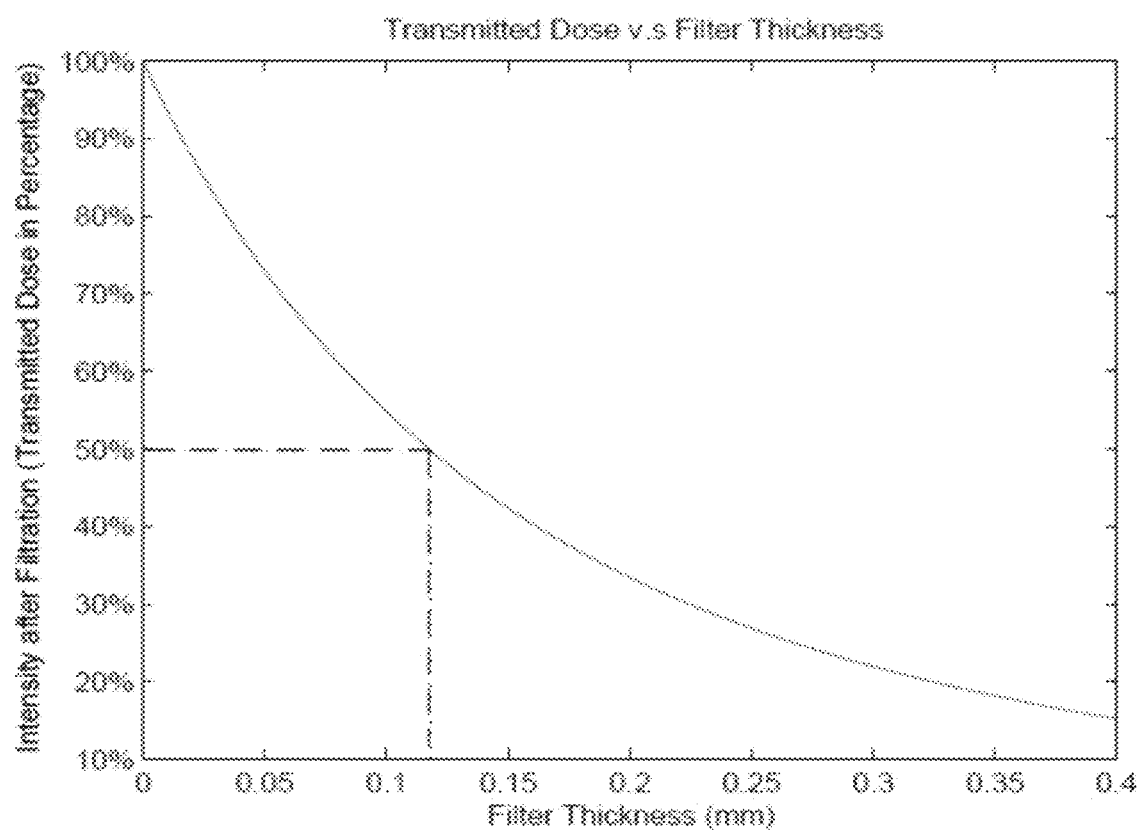

When ignoring tube power limitations, the precision improvement continues increasing with increasing Gadolinium filtration, though sublinearly, as shown in FIGS. 2A-B. FIG. 2A is a graph of the decomposition variance ratio as a function of filter thickness. FIG. 2B is a graph of transmitted dose as a function of filter thickness. Increasing the filtration thickness also increases the average spectral separation, leading to lower variance in the material decomposition if the mAs is increased to keep the dose constant. If we make the constraints that the transmitted dose reduction due to the filtration is no less than 50%, however, the precision improvement would be more than 40%. In other words, the dose efficiency would be increased by this amount if we maintained the same image quality.

Figure 3A:
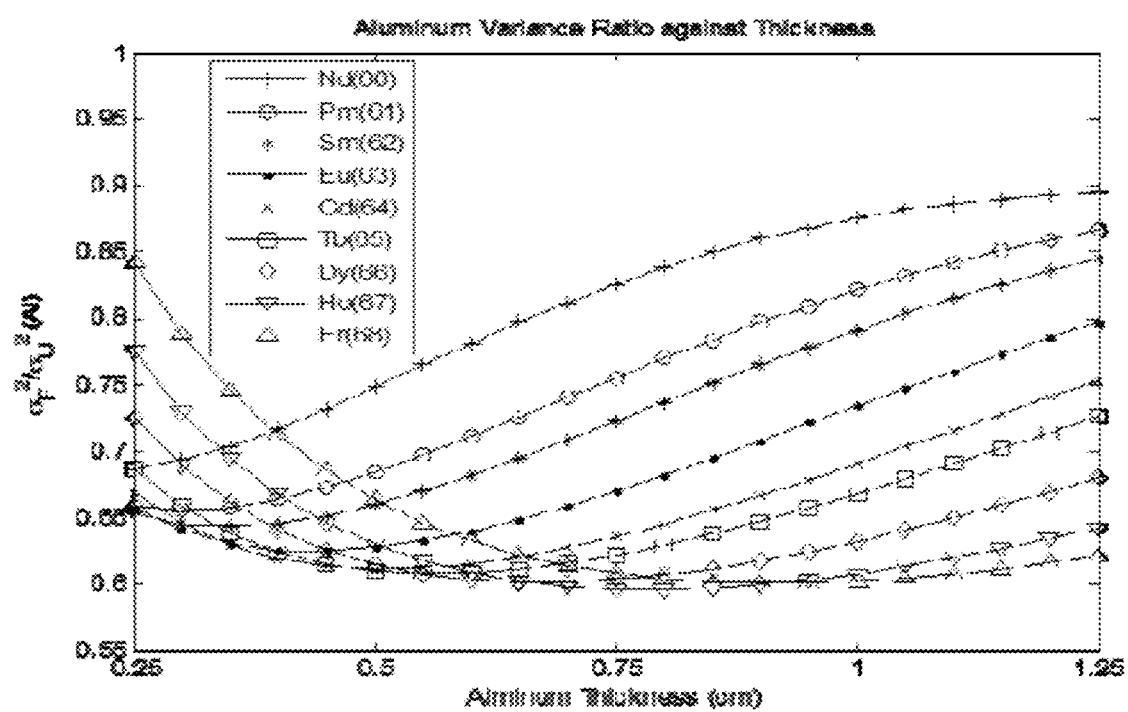
FIG. 3A is a graph of the decomposition variance ratio with filtration over without filtration with respect to aluminum thickness.
Figure 3:
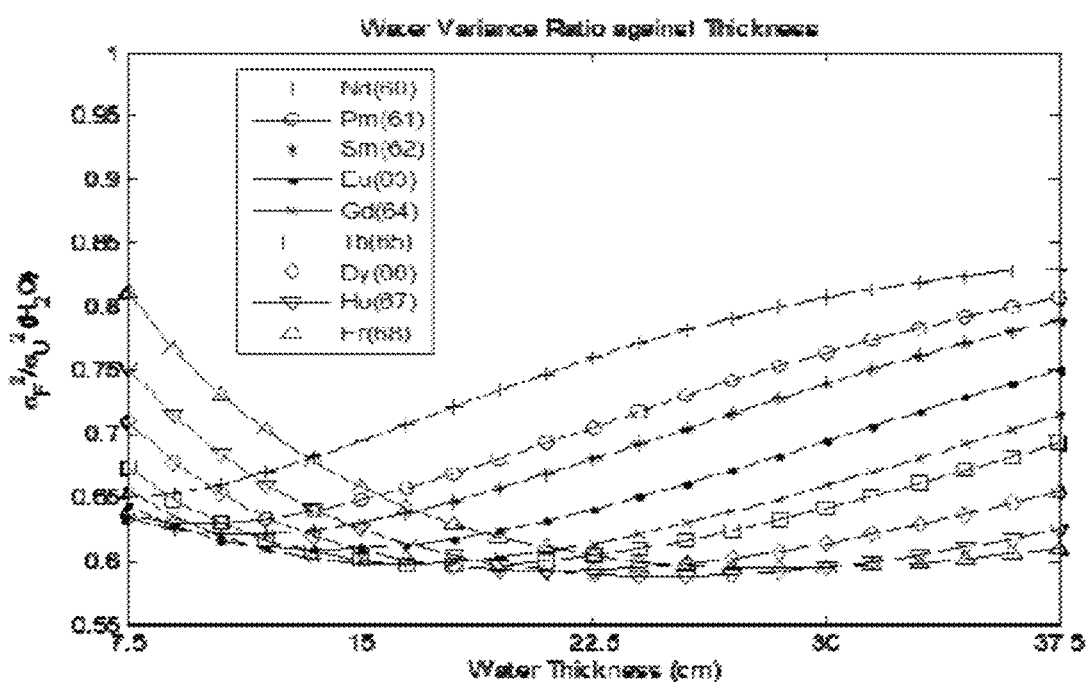
FIG. 3B is a graph of decomposition variance ratio with respect to water thickness. Potential filter materials perform variously at different object thickness. Data is collected from a mixture of aluminum and water and material decomposition is done using the phantom materials as basis. The thickness ratio of the water and aluminum is kept constant. Therefore FIG. 3A and FIG. 3B should be looked at simultaneously, since the horizontal axes of them are corresponding.

Since the selected optimal filter will likely be fixed during the scan, the consistency of the optimal material in terms of object thickness is another concern. To study this, we tested elements within the atomic number range of 60 to 68 individually at different object thicknesses. The pair of 0.5 cm Al and 15 cm water was the baseline thickness, and we set the object thickness range starting from a ratio of 0.5 to a ratio of 2.5 compared to baseline thickness while both object materials had the same ratio value in each case. This covers most clinical relevant thickness range. FIG. 3A is a graph of the decomposition variance with respect to aluminum thickness. FIG. 3B is a graph of decomposition variance with respect to water thickness. As revealed by FIGS. 3A-B, the performance of selected materials varies accordingly and each of them will have an optimal thickness value to have the maximum variance improvement. In practice, 1 to 2 unit thickness of aluminum and water object will be of more clinical interest, therefore, Holmium (Z=67) displays an overall balanced performance than the other materials. To be consistent, however, baseline object thickness will be studied for the rest of simulation. FIGS. 3A-B indeed shows that it is the optimal region where Gadolinium performs best.

In practice, we would like a filter material that is readily available and inexpensive, which Gadolinium satisfies. Instead of using pure Gd, we chose to use $Gd_2O_2S$, a common x-ray phosphor screen material, as our filter and studied its performance. The choice of $Gd_2O_2S$ over pure Gd was for economic reasons, and we will show below that it has a trivial difference on beam filtration. With the constraint that only 50% of the incident energy is lost to filtration, we would use 0.15 mm thick, 111.6 mg/cm$^2$ gadolinium oxy-sulfide.

Figure 4:
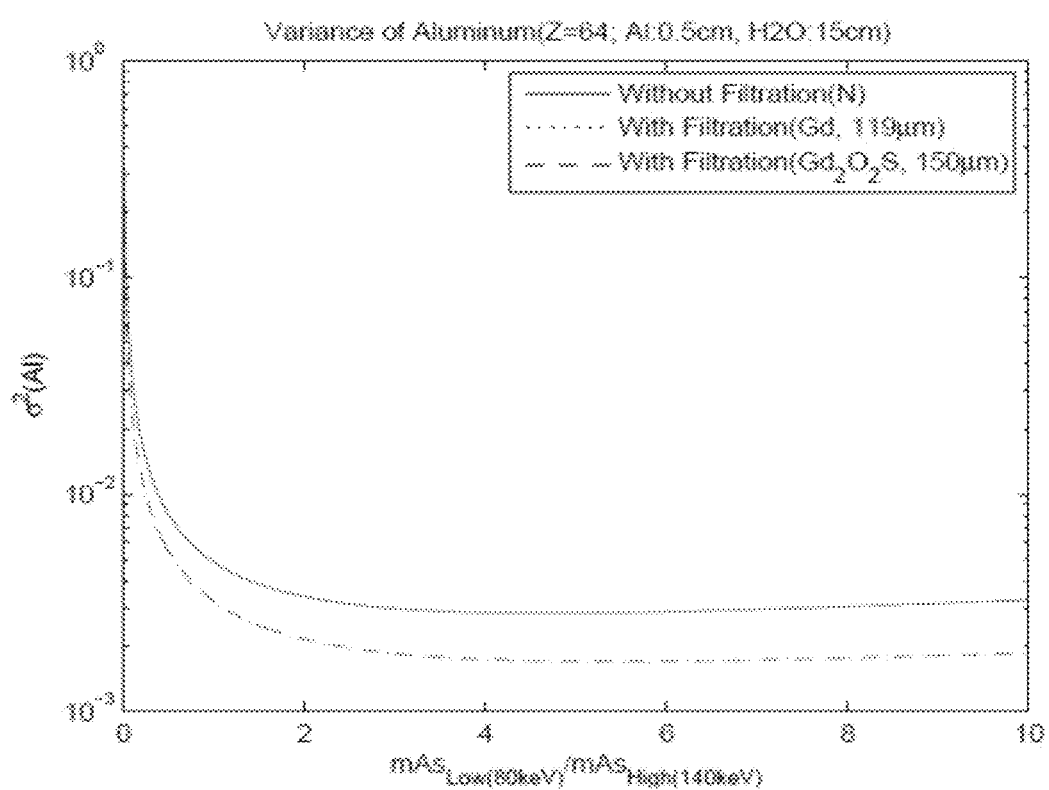
FIGS. 4A-B show the precision improvement with respect to different mAs ratio of low and high energies, when using 0.150 mm of $Gd_2O_2S$ (7.44 $g/cm^3$) and 0.119 mm of pure Gd as the filter. The curves of Gd and $Gd_2O_2S$ are almost undistinguishable, meaning that the two materials perform roughly the same, however $Gd_2O_2S$ is much cheaper and more readily available.
Figure 4:
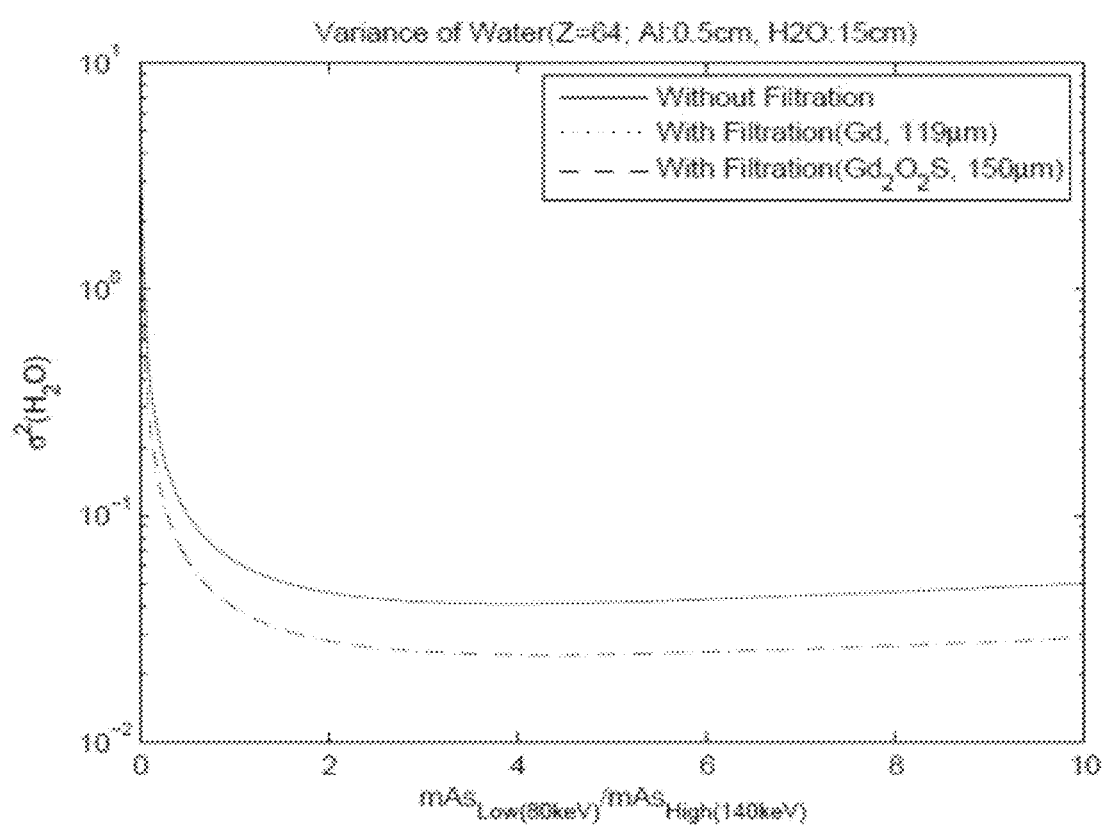

FIG. 4A is a graph variance in aluminum versus mAs ratio. FIG. 4B is a graph of variance in water versus mAs ratio. FIGS. 4A-B show the precision improvement when using 0.142 mm of $Gd_2O_2S$ (7.44 g/cm$^3$) as the filter. We can see that filtration due to $Gd_2O_2S$ and Gd are almost the same, yet the cost of $Gd_2O_2S$ is much lower than pure Gd. Also, the optimal mAs ratio for aluminum is about 5.4, while 4.3 is approximately the best choice for water. Hence, a mAs ratio of 5 is a reasonable compromise for both basis materials, especially since the minima of the curves are so broad.

TABLE 1

Spectral separation with or without filtration

| Energy | No Filter | $Gd_2O_2S$ |
|---|---|---|
| $E_{avg}$ | 57.2 keV (l)/75.0 keV (h) | 56.7 keV (l)/81.0 keV (h) |
| $E_{eff}$ | 53.3 keV (l)/65.5 keV (h) | 52.4 keV (l)/69.3 keV (h) |

From Table 1, it is clear that both the average energy and effective energy of the low and high kVp are increasingly separated after the filtration is applied. This result offers an intuitive explanation for the SNR improvement by adding filtration.

Other than a rapid kVp switching system, the dual source x-ray system has spectral separation concerns which could be solved by adding a different adaptive filter to each source. Before we started the experimental validation of the fixed $Gd_2O_2S$ filtration, we quickly simulated the dual source system with a tin filter applied to high kVp beam only. Given that the 50% loss of intensity due to filtration still held, we generated the basis material variance against mAs ratio plot for comparison of the two filtration strategy.

Figure 5:
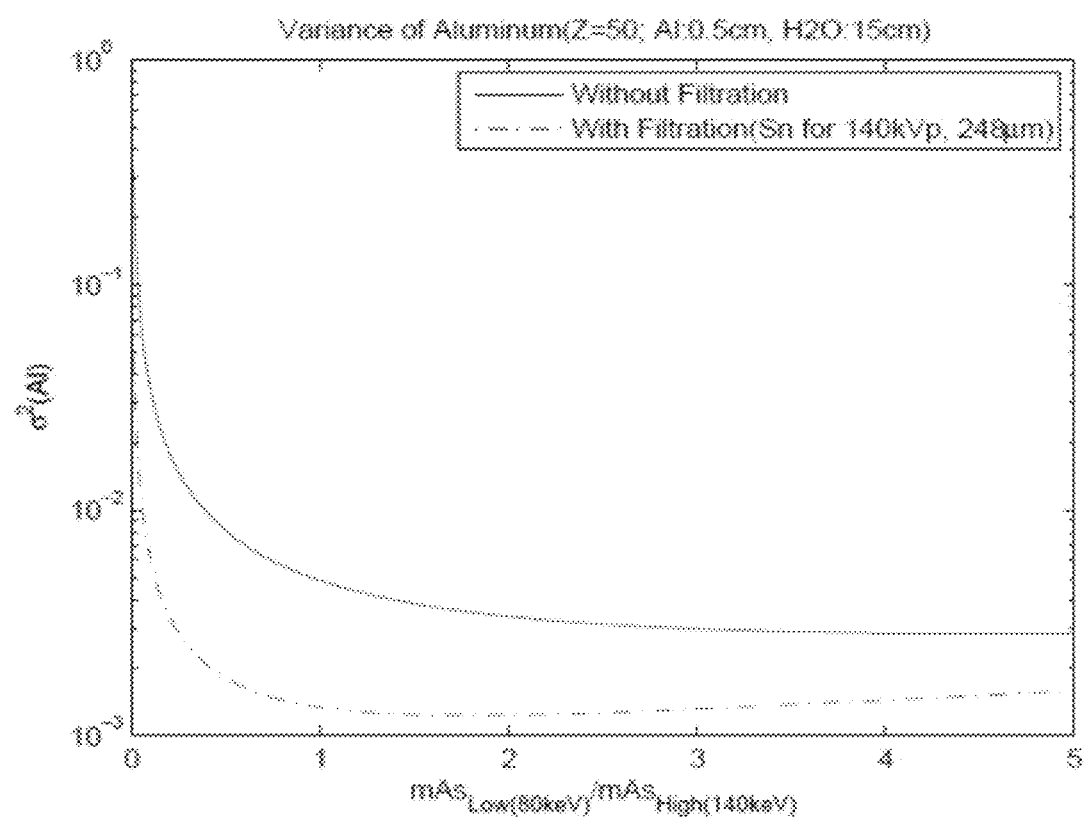
FIG. 5A is a graph of the variance of aluminum with respect to the mAs ratio provided by an alternative tin filter adapted to filter high energy spectrum only.
FIG. 5B is a graph of the variance of water with respect to the mAs ratio provided by an alternative tin filter.
Figure 5B:
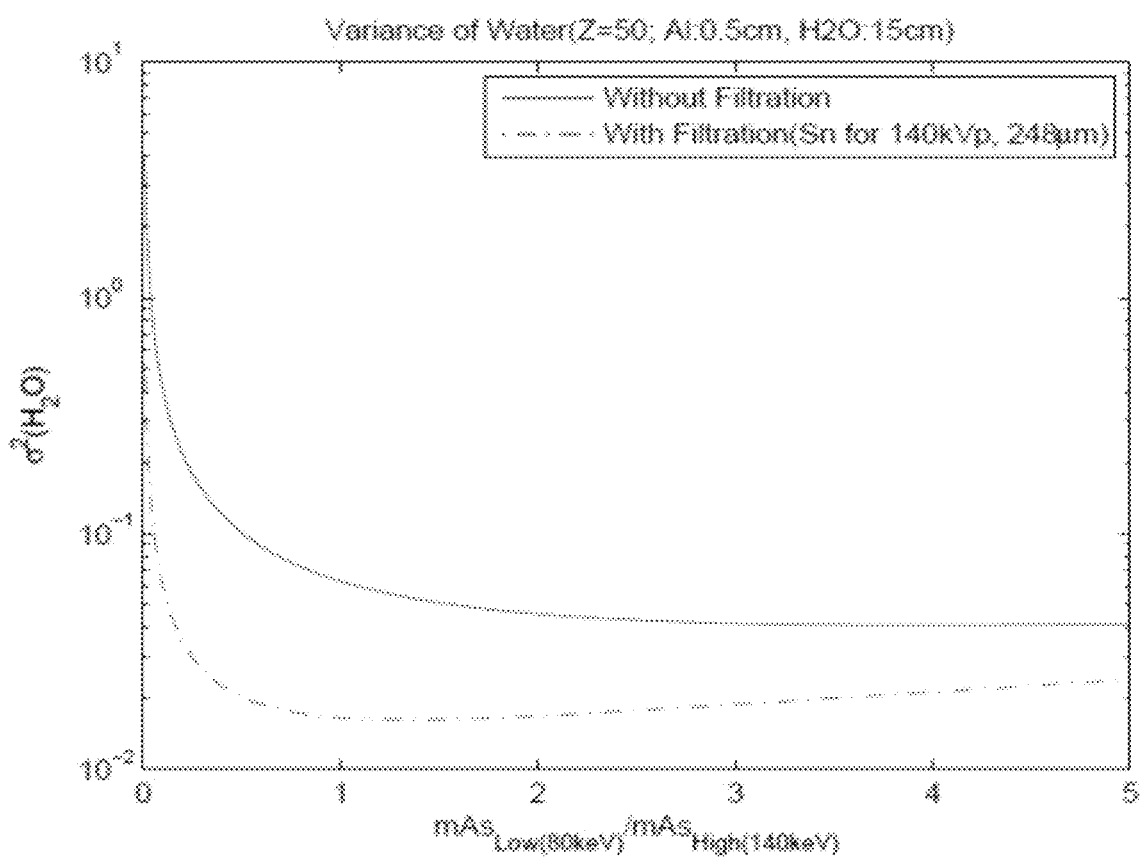
Figure 6:
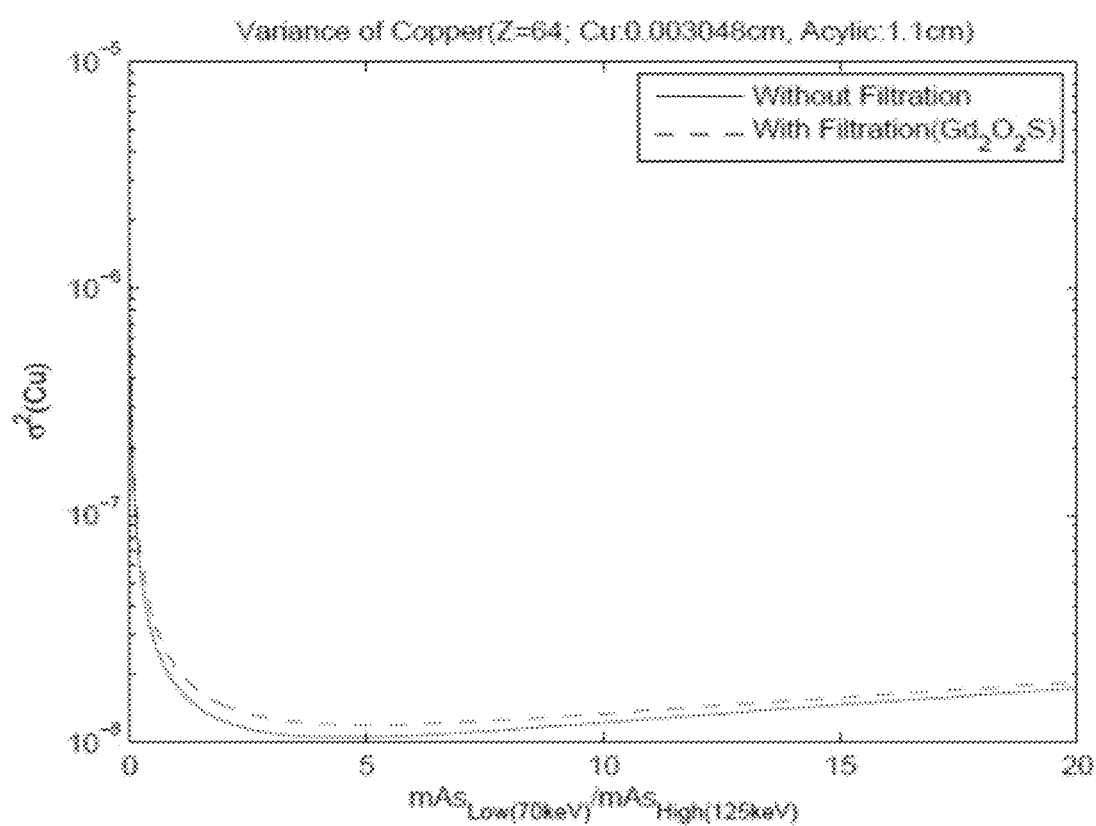
FIGS. 6A-H show the variance of decomposition vs. low/high energy mAs ratio, with and without $GD_2O_2S$ filtration for the four corners of the step wedge, by calculating the decomposition variance of each material (acrylic and copper) as a function of mAs ratio.
Figure 6:
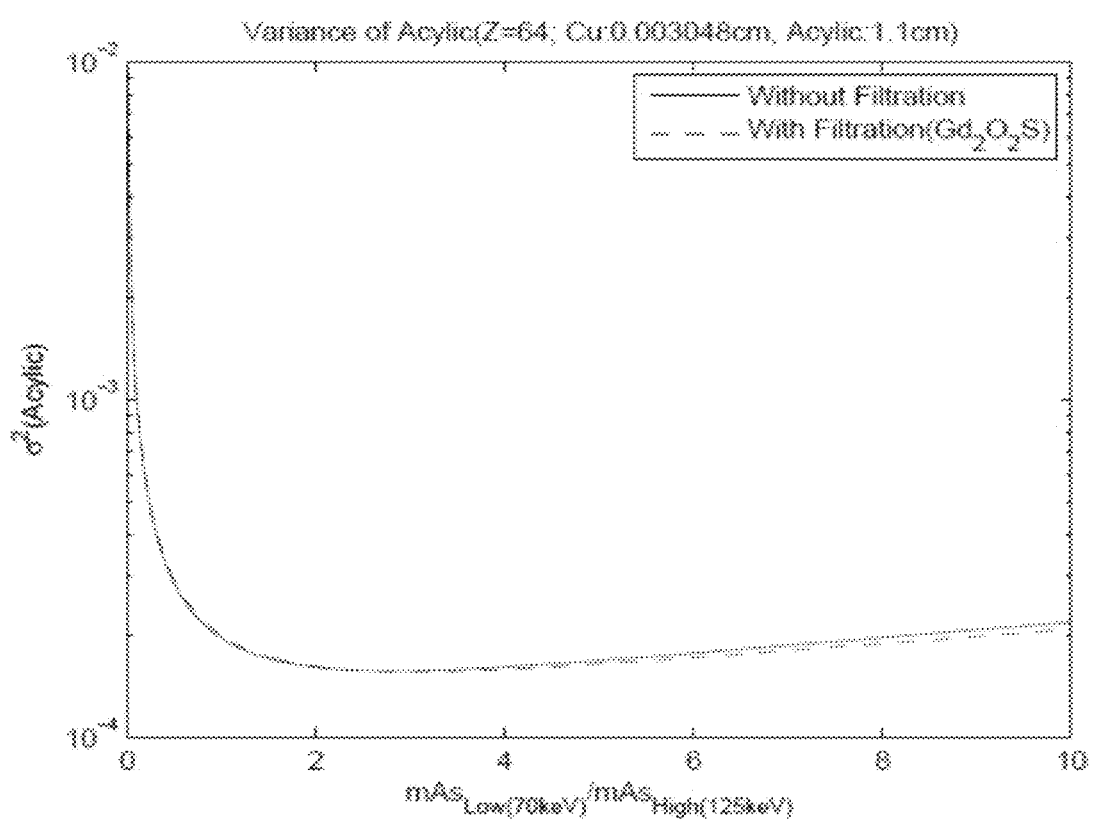
Figure 6:
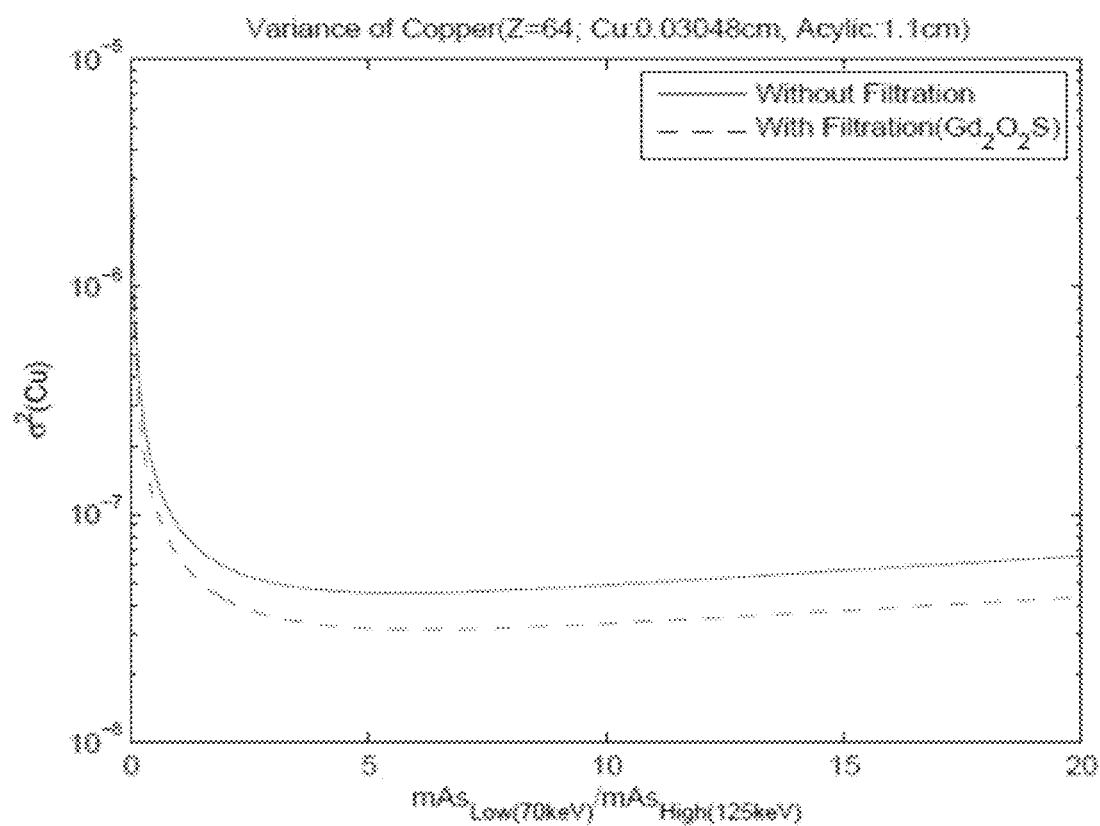
Figure 6:
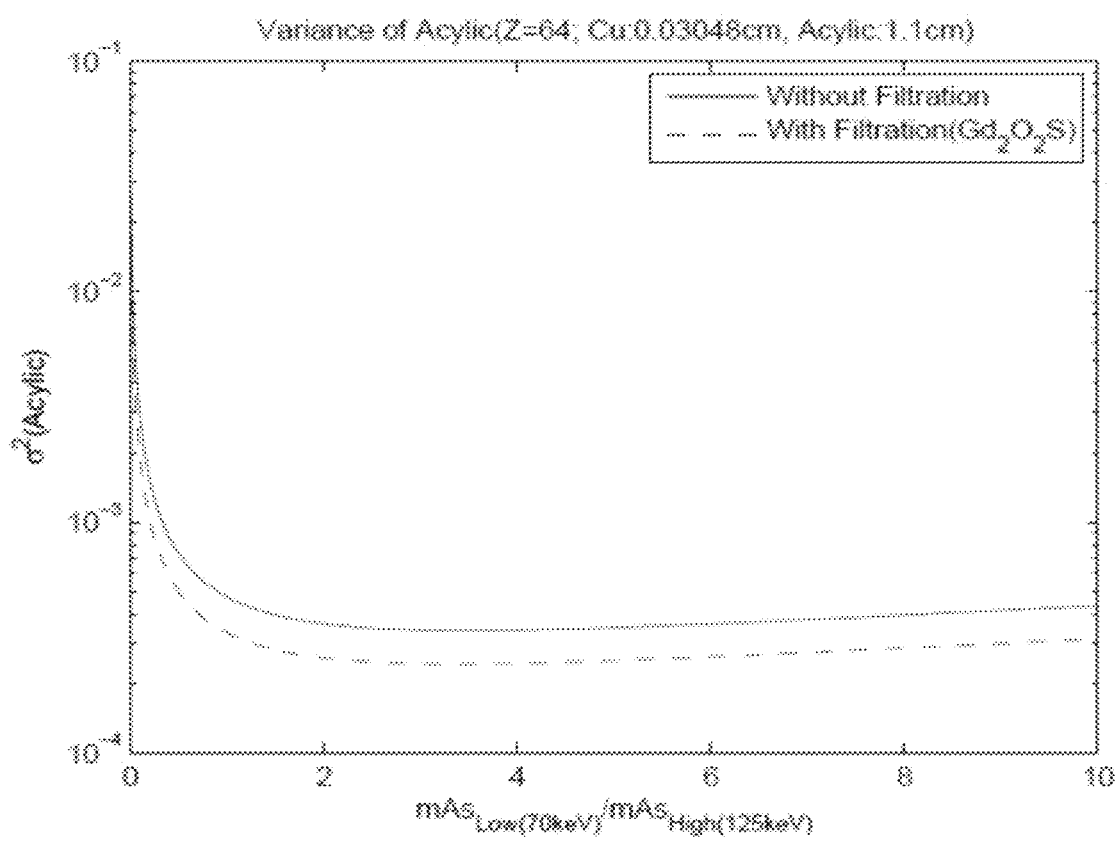
Figure 6:
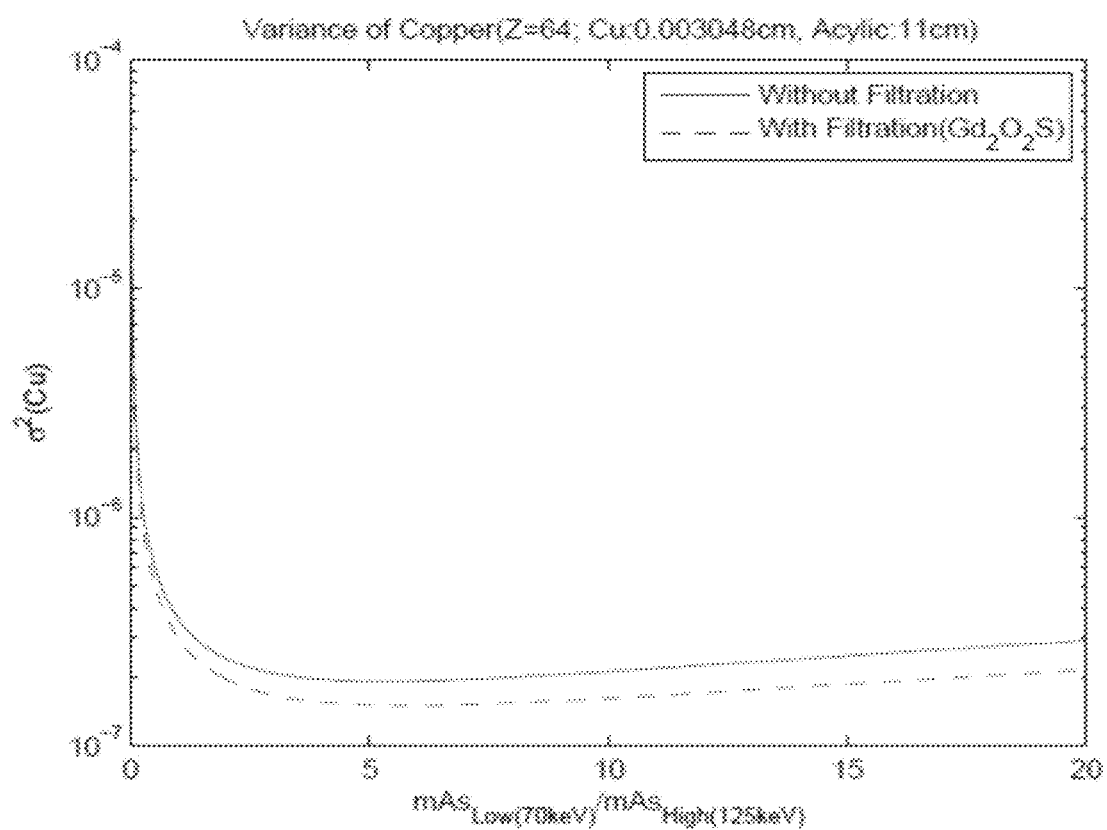
Figure 6:
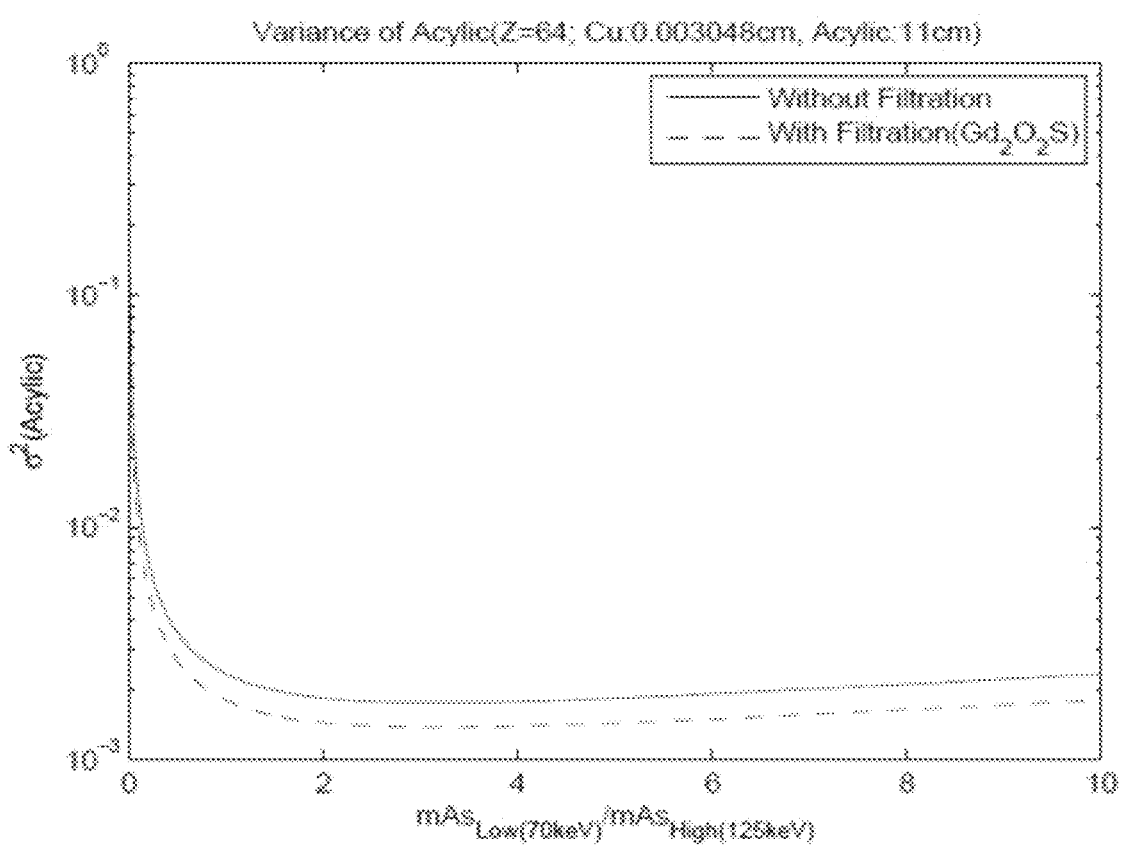
Figure 6:
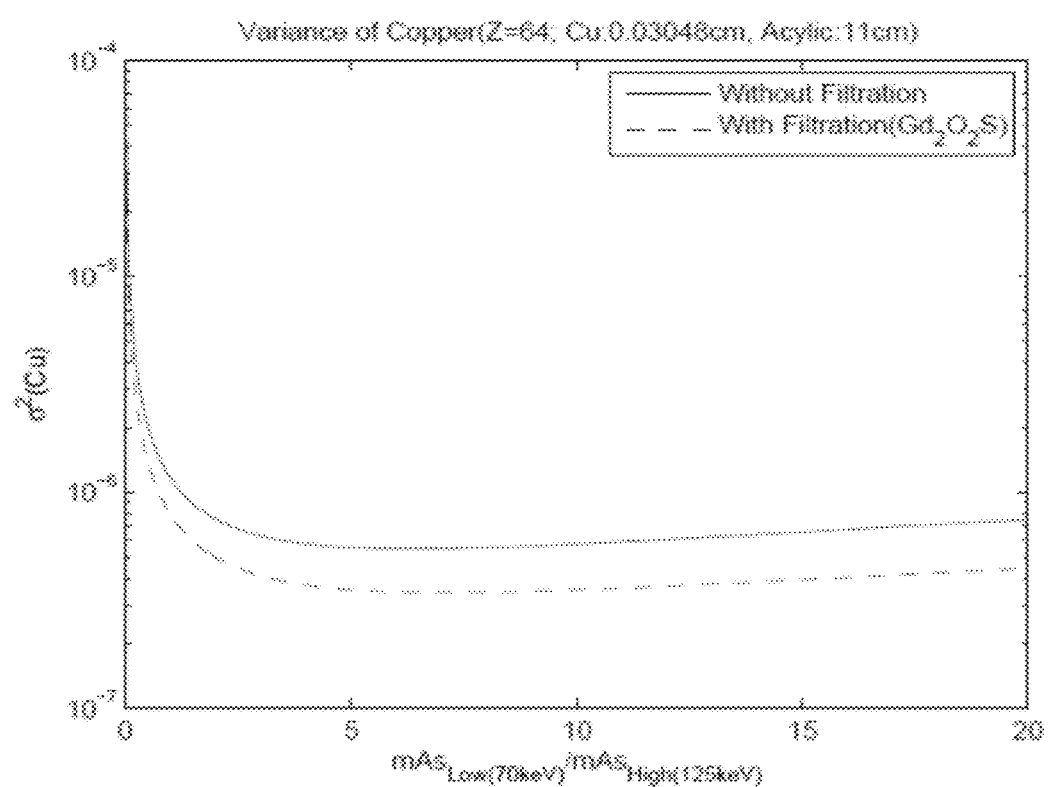
Figure 6:
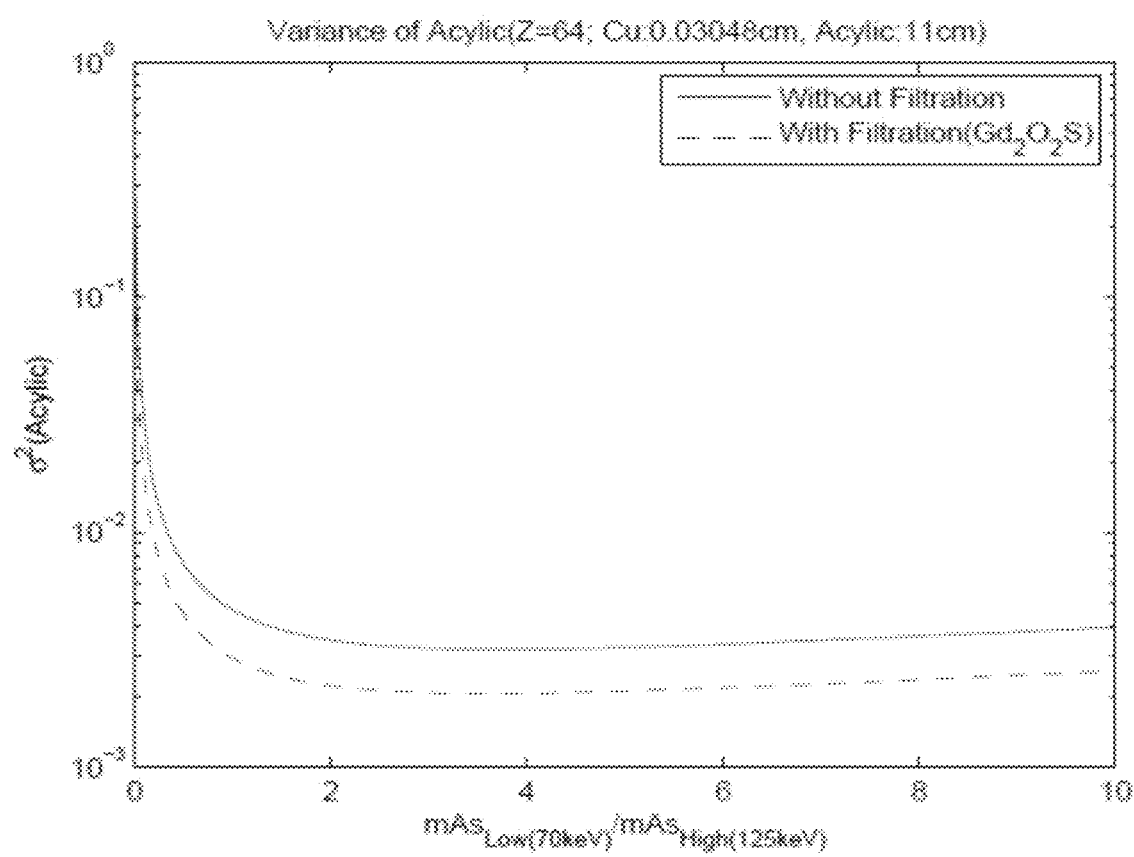

FIG. 5A is a graph of the variance of aluminum with respect to the mAs ratio provided by an alternative tin filter. FIG. 5B is a graph of the variance of water with respect to the mAs ratio provided by an alternative tin filter. As shown in FIGS. 5A-B, the performance of alternative tin filter on precision improvement is better than fixed Gadolinium filtration. Due to the beam-hardening effect of the adaptive tin filter on a high energy beam, it shifts the high energy spectrum further apart from low energy, therefore resulting in even better SNR improvement. Although the fast kVp switching system with a spectrum separation fixed filter has weaker precision performance, it will be less sensitive to physical displacement, without cross-scattering from two sources and is more economical.

Material and Methods

Based on the initial results of the efficacy of the fixed filtration, we chose $Gd_2O_2S$, a common x-ray phosphor screen material, as our physical filter to verify the simulation results on a benchtop x-ray system. A phantom composed of acrylic and copper was imaged with low and high energy spectra to compare the material decomposition precision with and without the filter.

The benchtop's Varian G-1593BI x-ray tube has a maximum allowable voltage of 125 kVp. We were therefore unable to test our initial simulation results, which were based on 80 and 140 kVp spectra to reflect clinical settings. Nonetheless, we were still interested in the potential benefit of a K-edge filter even for dual energy spectra at lower energy. Hence, we operated the x-ray tube at 70 and 125 kVp to maintain the separation of the spectra. The imaged phantom was a two dimensional step wedge (10 steps in each direction), composed of acrylic sheets (1.1 cm thick) and copper tape (30.5 µm thick), which are stepped in directions orthogonal to each other. The phantom therefore had a 10×10 grid of acrylic-copper thickness pairs. Using fluoroscopy mode, data was collected by a PaxScan 4030CB flat-panel detector (Varian Medical Systems, Palo Alto, Calif.) after gain, offset and bad pixel corrections were applied. The detector was operated in 2×2 binning mode, resulting in 1024×768 pixels per projection. Each pulse width was 13 ms and the frame rate was 15 fps (frames per second). A DRZ-Plus screen (MCI Optonix, Washington, N.J.) was used as the $Gd_2O_2S$ filter (100 mg/cm$^2$ $Gd_2O_2S$, of which 83% is Gd by mass) by placing the screen in front of the collimator. Since the pulse width was fixed in fluoroscopy mode, radiation dose was controlled by using different tube currents (mA). The tube current of the low/high energy projections was adjusted to 20 mA (l) 110 mA (h) without filtration and 56 mA (l) 128 mA (h) with filtration. While the mAs ratio of 2 was maintained, the mA was increased by a factor of 2.8 to ensure that the total dose with and without filtration were approximately the same. Although we had expected this filtration to require approximately a factor of 2 increase in mA to maintain the same exposure to the phantom at 80/140 kVp, the lower kVp used here requires a larger increase in mA. A Radcal 9010 pancake ionization chamber was used to measure the exposure rate (mR/s) at the phantom.

As discussed for FIGS. 4A-B, a low/high energy mAs ratio of five was deemed to be an appropriate selection to get lower variances of both material decomposition. We checked its validity with the phantom experimental settings as shown in FIGS. 6A-H, which show the variance of decomposition vs. low/high energy mAs ratio, with and without $GD_2O_2S$ filtration for the four corners of the step wedge, by calculating the decomposition variance of each material (acrylic and copper) as a function of mAs ratio. The thickness pairs at the four corners of our step wedge phantom were simulated. The optimal ratio for acrylic [FIGS. 6A-D] ranges from 3 to 3.7, while that of copper [FIGS. 6E-H] ranges from less than 5 to over 7.5. For clinical applications, we would be more interested in the filter performance in thicker parts of the phantom since they are more representative of the patient attenuation and the noise will be much larger than the less attenuating regions where SNR should be high. Therefore, a mAs ratio of 5 is still an appropriate choice for the experiment.

The real experimental mAs ratio of low and high energy, however, was approximately 2 due to the system limitation. Nevertheless, we could artificially make the raw images of having mAs ratio of 5 by data post-processing. The method is to average five frames of low energy fluoroscopy images and two frames of high energy. Since the signal intensity is linear with the mAs of each scan, so is the Poisson noise (electronic noise is ignored as mentioned). By doing average processing, the same signal intensity will be maintained, but the standard deviation will decrease because it is the square root of noise (or variance). Hence, we would get images with better SNR, as we could have gotten using higher mAs and to achieve the quasi-mAs ratio of 5.

Both phantom and air scans were done with and without filtration. To avoid the effect of detector lag during the flouro-mode, we collected 1,000 frames of images in total for each scan and selected every tenth one to make a data set of 100 frames for evaluating decomposition noise. The log-normalized detected intensities within each cell of the 10×10 grid were first averaged. The averaged low and high line attenuation values ($L_l$ and $L_h$) were used to find the third-order polynomial fit to the known thicknesses of the two materials. Separate polynomial fits had to be performed for the filtered and unfiltered data. Then material decomposition was done per pixel and frame by pairing up low and high energy frames so that the mean and variance of the decomposition could be computed for each thickness pair. To avoid spatial correlations in the precision evaluation, we first calculated the variance of each pixel along the 100 frames and then averaged these temporal variances within the same cell to get a map of precision across the phantom. We made the number of pixels from each cell the same during this process. Additionally, the data at the edge of each grid cell was discarded from the calculation to avoid misregistration artifacts, which arose from small differences in phantom placement between the low and high energy scans. Nonetheless, the data loss does not affect the statistical significance of the results since we still had 900 pixels per grid cell.

Simulations were done in parallel to compare with and verify the experimental results. The simulation parameters matched the experimental settings.

Results and Discussion

Table 2 lists the experimental parameter settings and the detected exposure rates of the phantom. The low/high energy mA ratio with and without filtration was fixed at 2. Ideally, exposure rate is linearly proportional to the tube current, given the same kVp and filtration. To make sure the dose of the low, high, and their sum were approximately the same in the two situations, 20 mA (1) 110 mA (h) was chosen without filtration while the mA was increased by 2.8-fold after the DRZ-Plus screen ($Gd_2O_2S$) was inserted to achieve similar exposure rates (as measured by the ion chamber).

TABLE 2

Experimental Set-up and Exposure Detection

| Filtration | Tube Voltage (kVp) | Current (mA) | Exposure Rate (mR/s) |
|---|---|---|---|
| None | 70 | 20 | 77.4 |
|  | 125 | 10 | 164.4 |
| $Gd_2O_2S$ | 70 | 56 | 76 |
|  | 125 | 28 | 167 |

Figure 7:
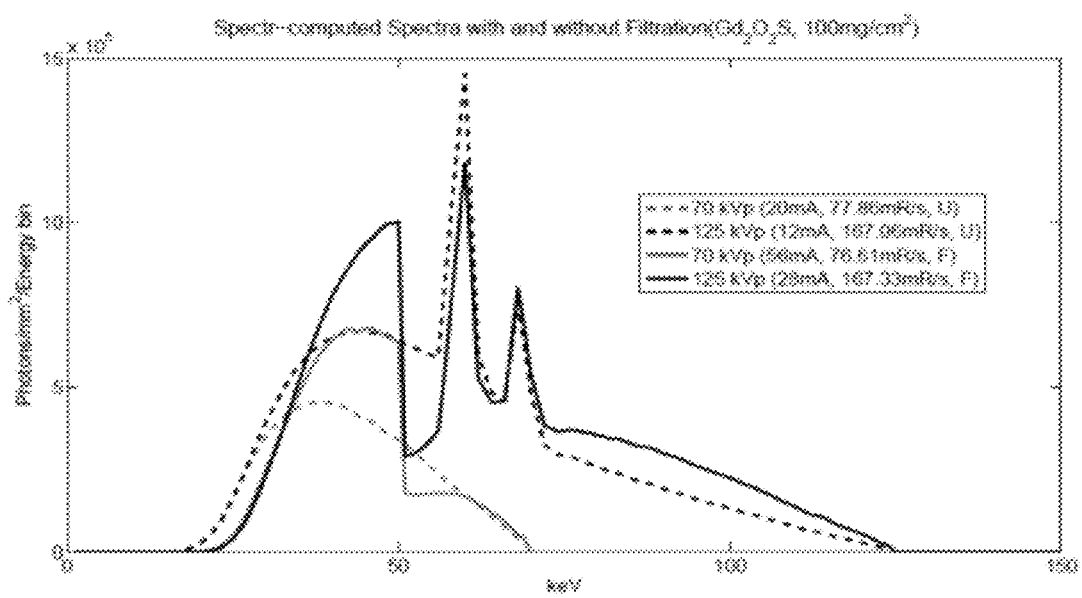
FIG. 7 shows the simulated spectra with and without filtration that match the experimental kVp and exposure rates, computed from Spektr.
Figure 8:
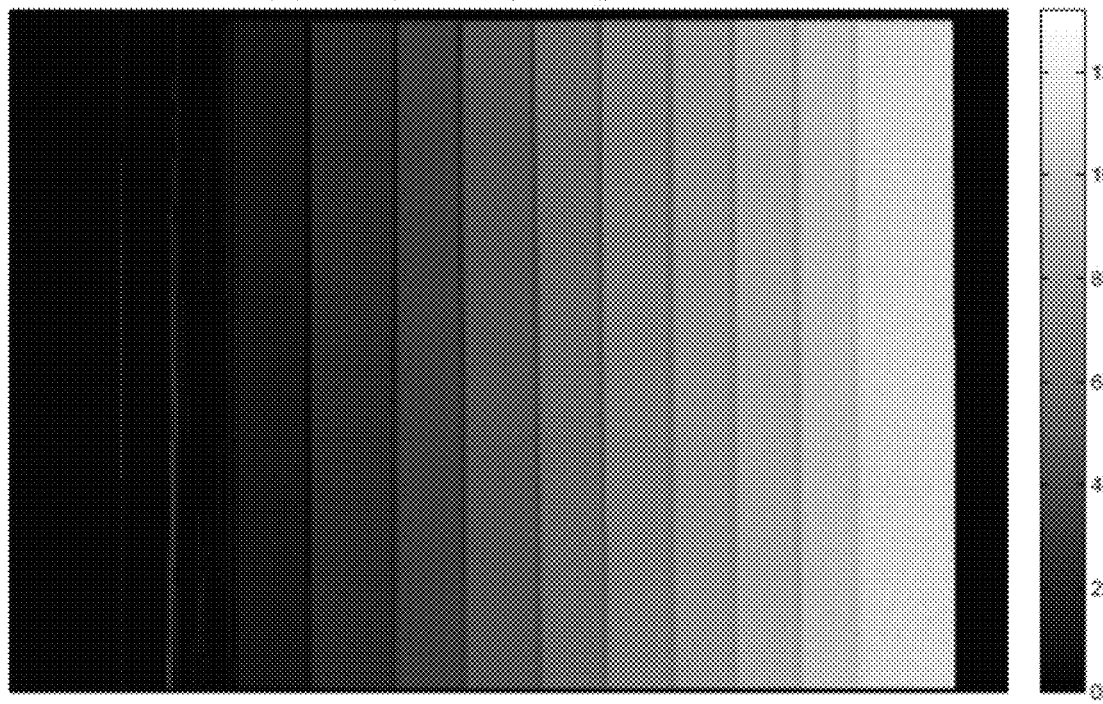
FIGS. 8A-D show decomposed images of acrylic and copper (cm) with (F) and without $Gd_2O_2S$ filtration (U). Data is collected experimentally.
Figure 8:
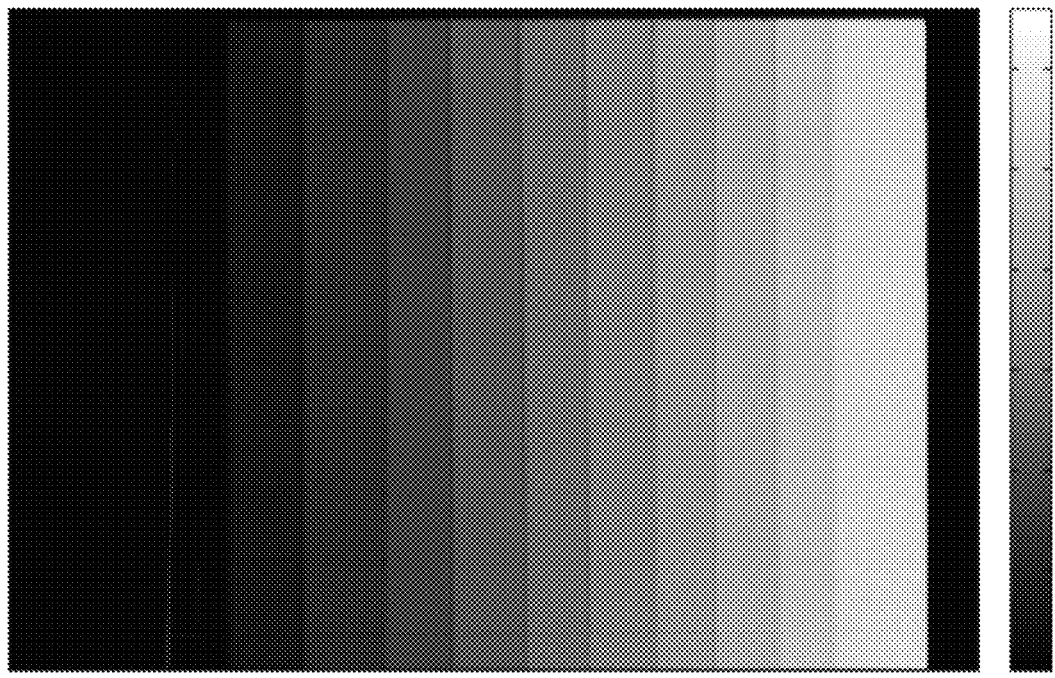
Figure 8:
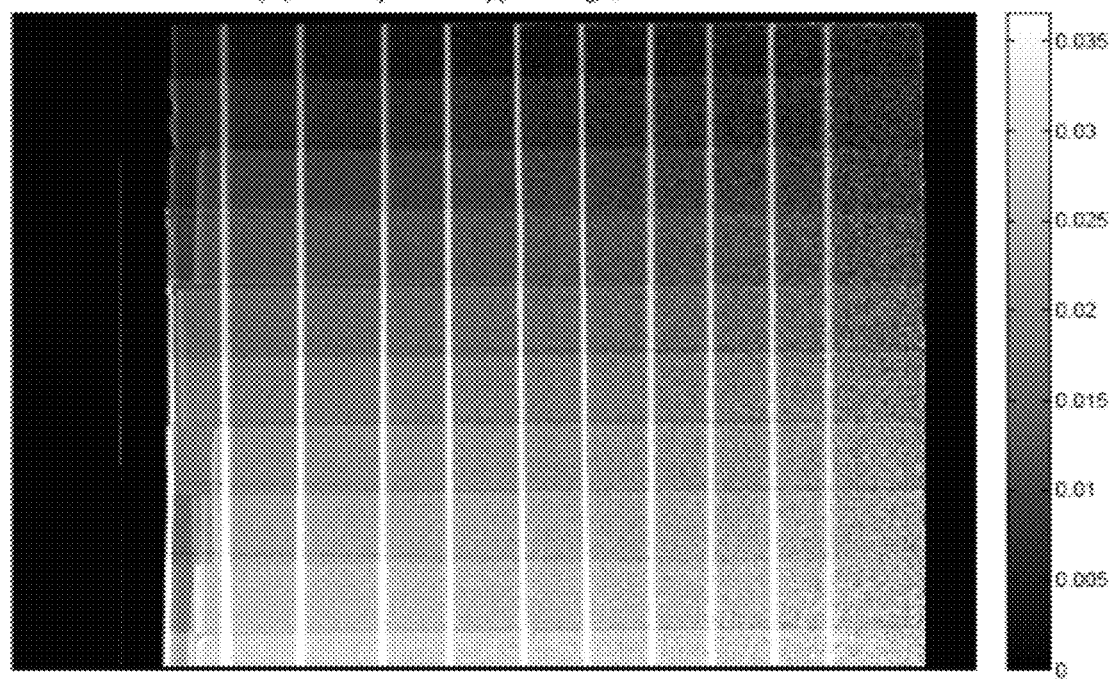
Figure 8:
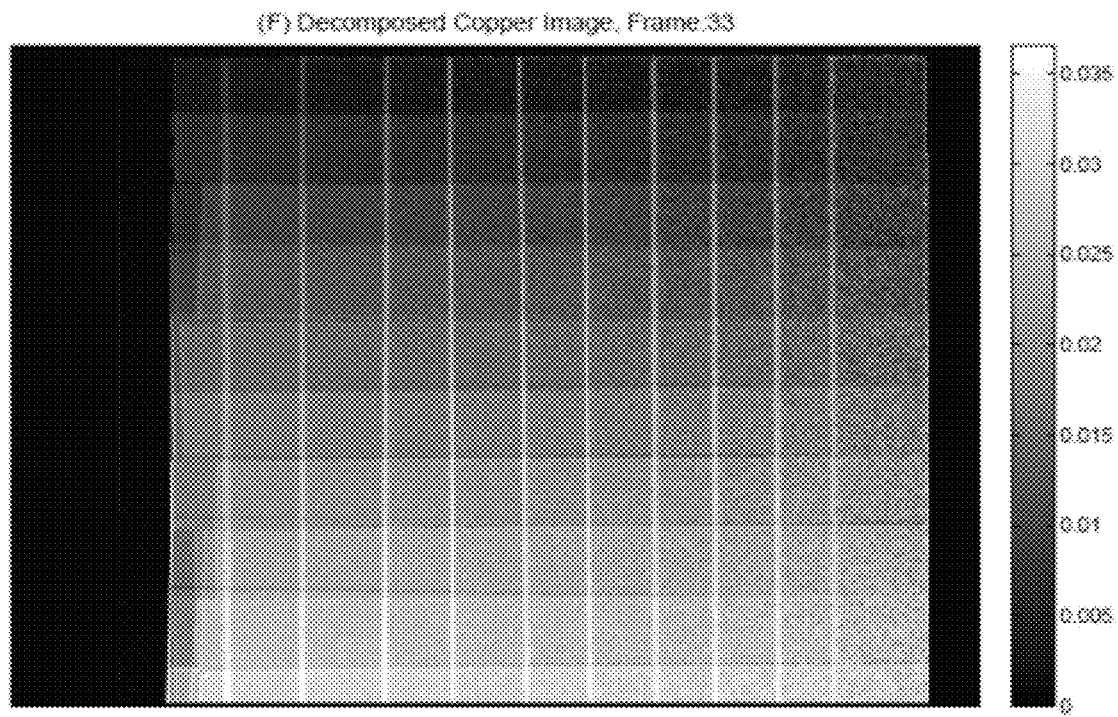
Figure 9A:
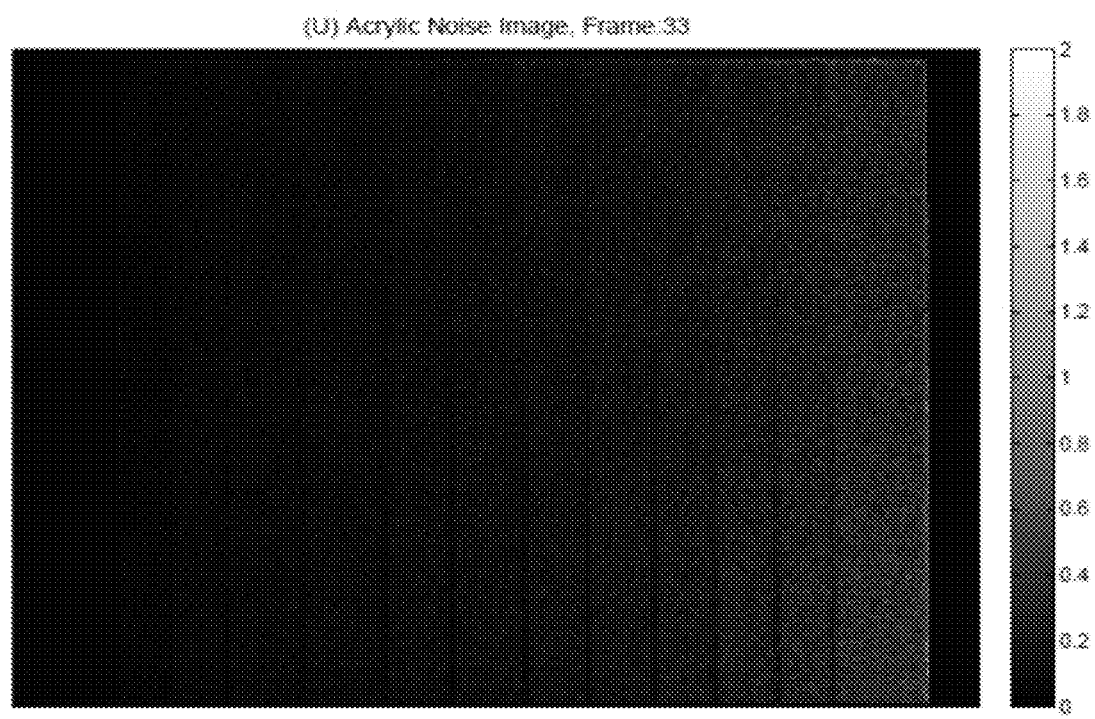
FIGS. 9A-D show the absolute value of the error (cm) of the acrylic and copper decomposed images with (F) and without $Gd_2O_2S$ filtration (U).
Figure 9:
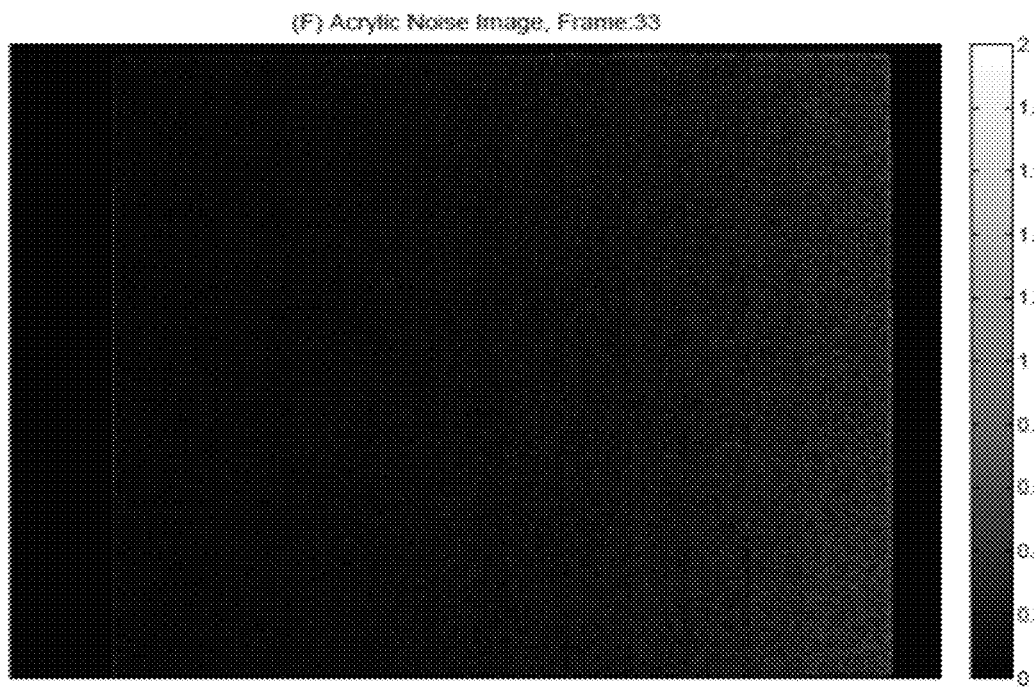
Figure 9:
Figure 9:
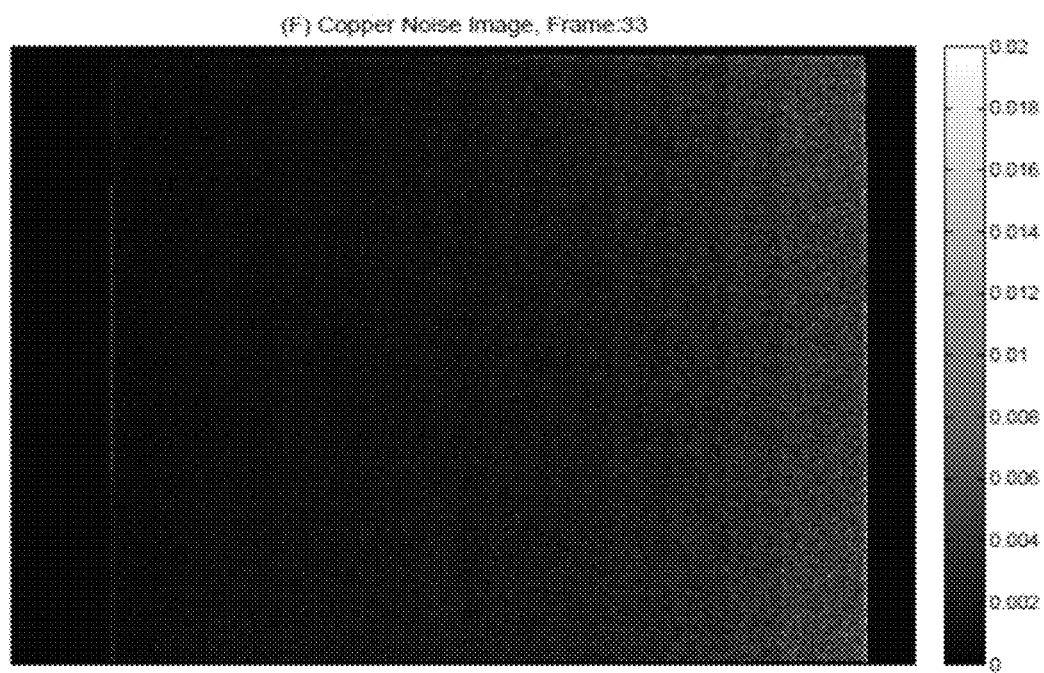

FIG. 7 shows the simulated spectra with and without filtration that match the experimental kVp and exposure rates, computed from Spektr. The K-edge effect is easily recognized from the filtered curves, marked with an 'F' in the legend. The computed exposure rates closely approximate what was measured except for the case of 125 kVp without filtration. The simulation showed that 12 mA instead of 10 mA would be needed to deliver the same exposure rate as what was detected. This divergence might largely be due to the inaccuracies of the x-ray tube within the lower current range at high energy. Nevertheless, since the individual exposure rates and their sum were about the same after making this adjustment, the simulation should be valid for predicting the precision improvement of the spectrum separation fixed filter.

The acrylic and copper decomposition images (units of cm) based on the dual energy experimental data are shown in FIGS. 8A-D, which show decomposed images of acrylic and copper (cm), where the acrylic steps are increasing from left to right, while the copper steps are increasing from top to bottom, and where misregistration between the low and high energy scans adds a grid-like structure to the images. Filtration is denoted by '(F)' while '(U)' denotes the unfiltered case. After decomposition, the thicker each material is, the higher attenuation it has and the brighter it appears in the images. Therefore, we can see from the two material decomposed images, that the acrylic stacks were overlapped along the horizontal direction to make the step wedge, while the copper steps were aligned vertically with increasing thickness from top to bottom. The frame number (#33) was arbitrarily chosen and is representative of the other frames. The strips between each acrylic step were due to the misregistration of the projection images at the two energies. We can visually assess that the noise decreased for both the acrylic and copper images when using the $Gd_2O_2S$ filter.

By subtracting the 33$^{rd}$ frame from the average of the 100 frames and taking the absolute value, we can better compare the noise in the images as shown in FIGS. 9A-D, which show the absolute value of the error (cm) of the acrylic and copper decomposed images. It is much clearer that the noise levels of both the acrylic and copper images decreased with $Gd_2O_2S$ filtration. The bright pixels along the left and right edges were due to detector non-linearity and the discontinuity of the phantom.

Figure 10:
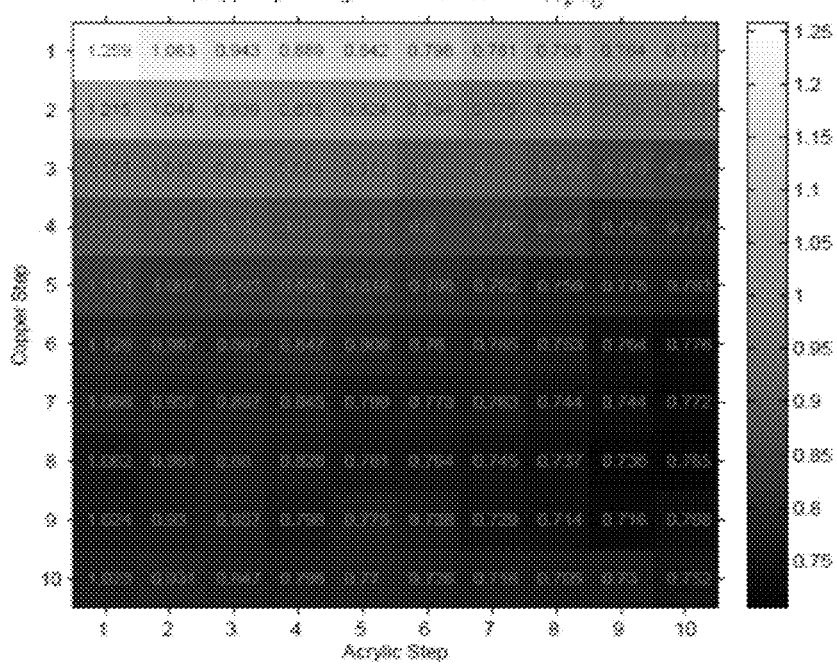
FIGS. 10A-D show variance reduction of acrylic (FIGS. 10A, C) and copper (FIGS. 10B, D) images after filtration is applied, for experimental data (FIGS. 10A, B) and simulation data (FIGS. 10C, D) at corresponding acrylic and copper thicknesses.
Figure 10:
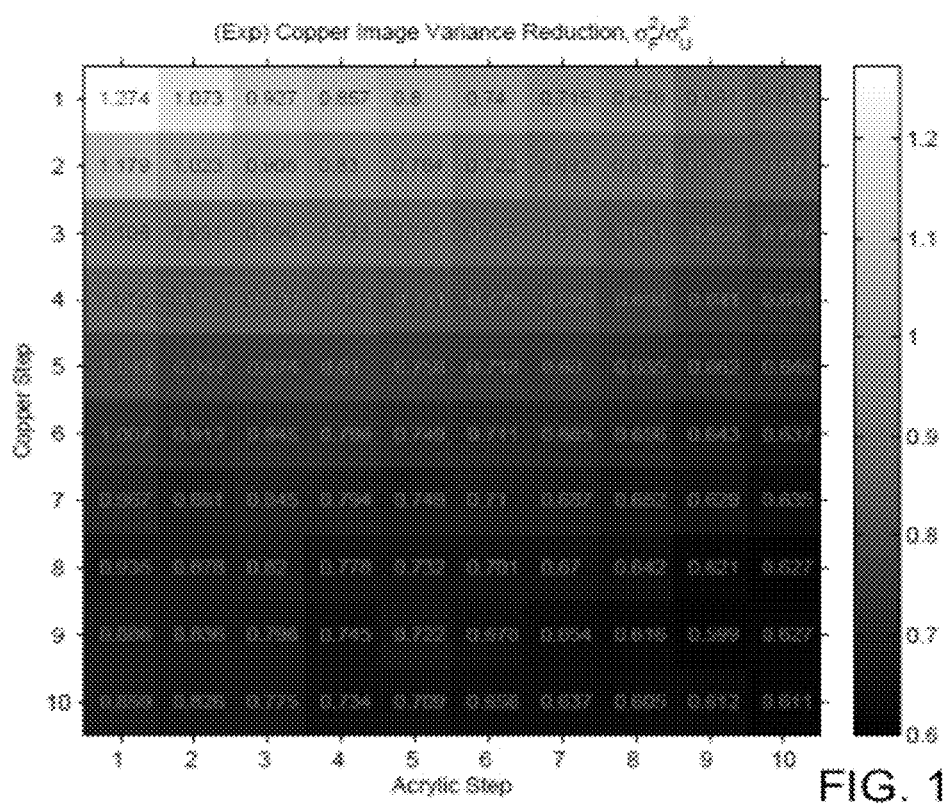
Figure 10:
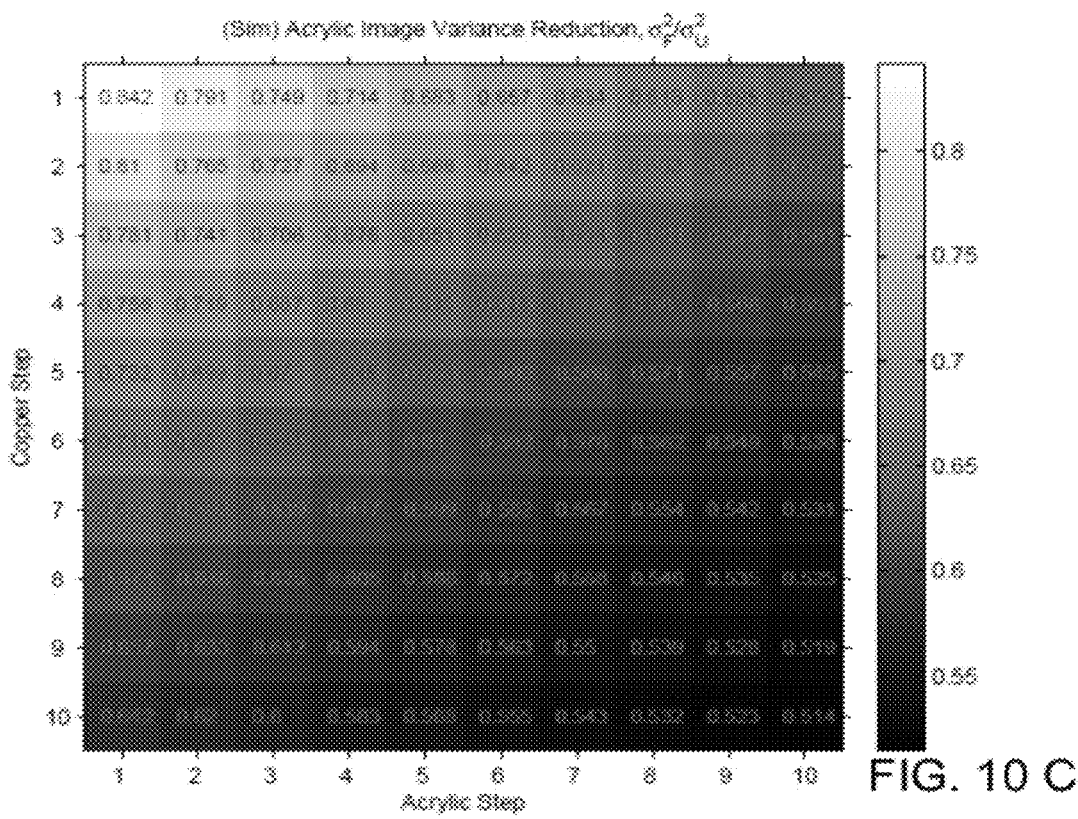
Figure 10:
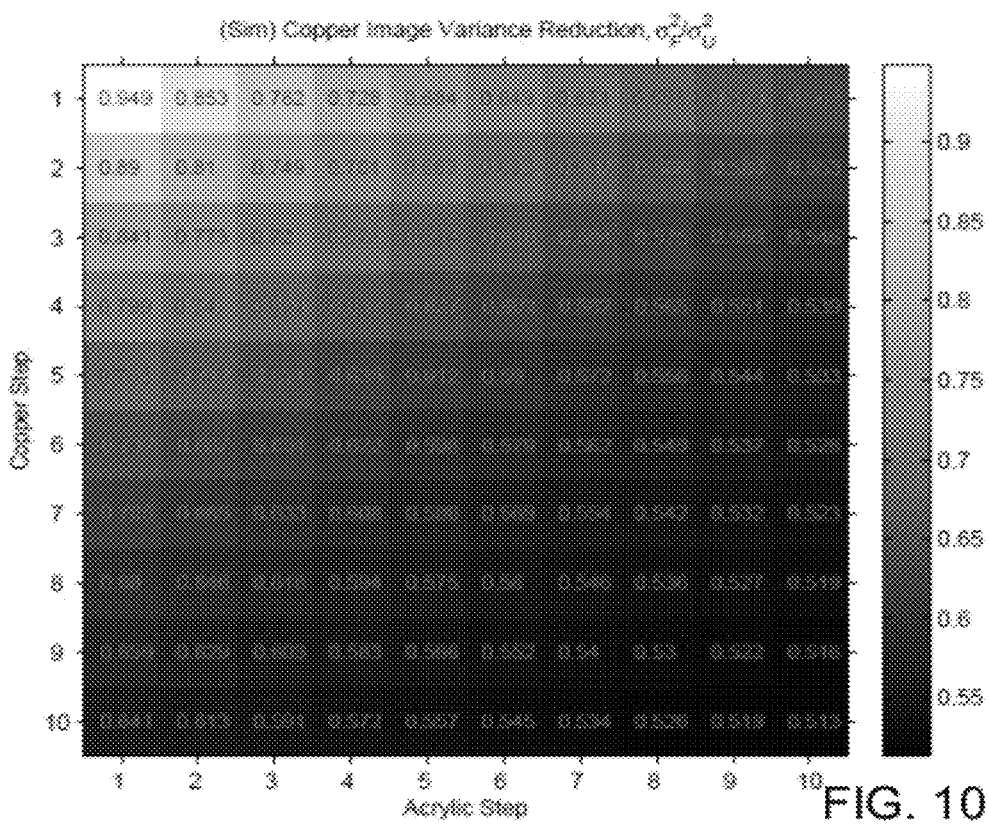

The variances of the material decompositions of each thickness pair were calculated for the experimental and simulated data. The ratios of variances from the filtered to unfiltered decomposed images are shown in FIGS. 10A-D, which show variance reduction of acrylic (FIGS. 10A, C) and copper (FIGS. 10B, D) images after filtration is applied, for experimental data (FIGS. 10 A, B) and simulation data (FIGS. 10C,D). Experimental results are denoted as '(Exp)' while '(Sim)' denotes the simulation data. Clearly, a ratio of less than 1 indicates that the filter reduces decomposition noise and increases the precision. The experimental result shows that for both materials, the ratio generally decreases from the top left to bottom right. At thicker areas, the variance reductions are approximately 25% for acrylic and 40% for copper. That is, as the phantom becomes more attenuating (due either to the copper or acrylic), there is more benefit from the filter. This is compatible with the simulated results, which display a monotonic decrease of the ratio from the top left to bottom right. The variance reduction based on simulation, can reach almost 50% at thicker areas. Recalling the simulation results shown in FIGS. 3A-B, it indicates the performance of metallic Gd would become worse if the object keeps getting thicker but the object thickness in this experiment was not large enough to observe this. Comparing the experimental results with this, it reveals that even at the thickest part of the step wedge, the copper and acrylic thickness is still within the region that Gd filtration will help improve the variance more and more. Yet we could imagine that if the step-wedge phantom gets thicker, sub-quadratic trend, i.e. decreasing first and then increasing, will show along the diagonal line of this variance reduction map, rather than the observed monotonic behavior.

The variance ratios from the simulation suggest that decomposition noise would decrease across the entire phantom by using filtration, however, in the experimental results the noise increased in the less attenuating region of the phantom with an overall lower improvement than expected from the simulation.

Further study is needed to explain the non-monotonic decrease of the ratio with increasing thickness from the experimental results as well as the higher than expected ratio from the simulated results. The ratio was 17-37% higher for acrylic and 11-27% higher for copper. One possibility is the effect of electronic noise and other additive noise that may have been overlooked since only Poisson noise was modeled in the simulation. The other factor that might cause worse experimental performance is the strong scattering of this table-top system.

Figure 11A:
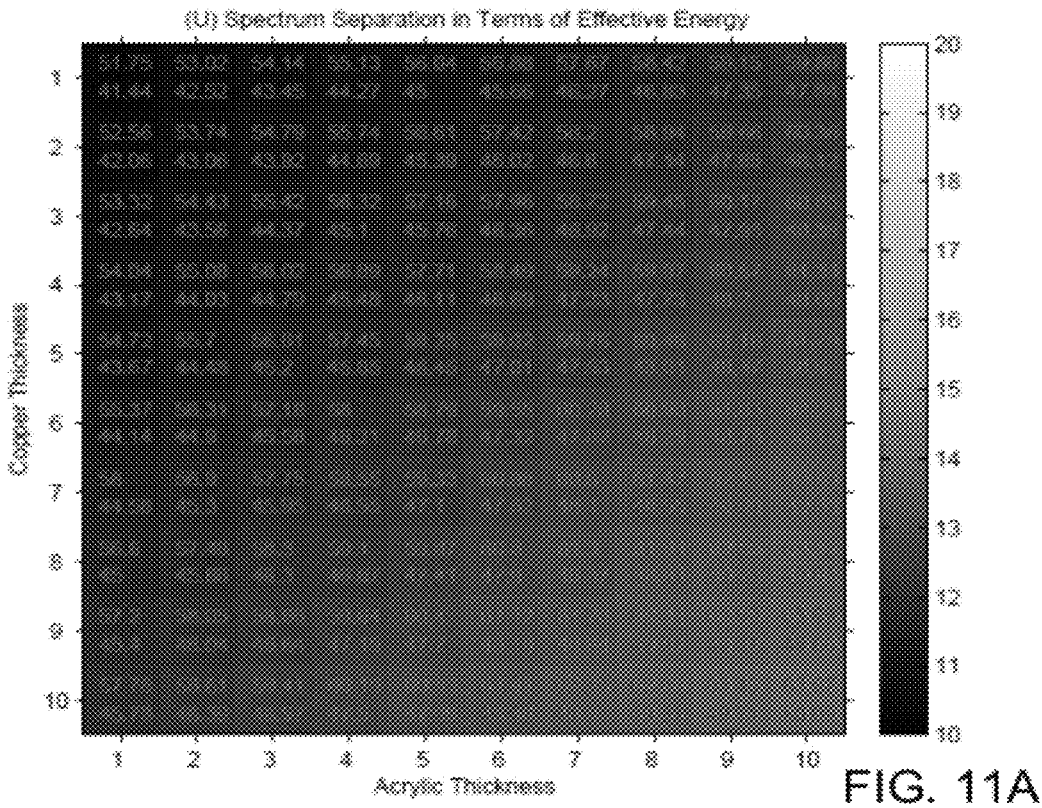
FIGS. 11A-C show that filtration increases the energy separation between the low and high energies. Effective energy is calculated and shown here based on simulation.
Figure 11:
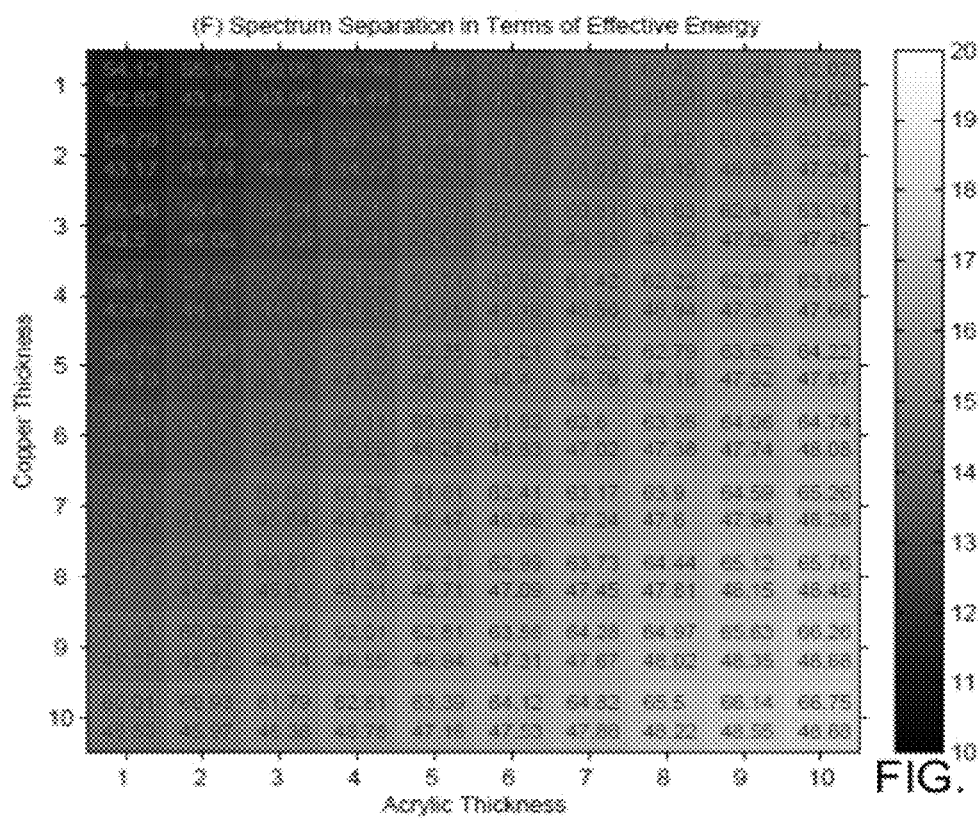
Figure 11:
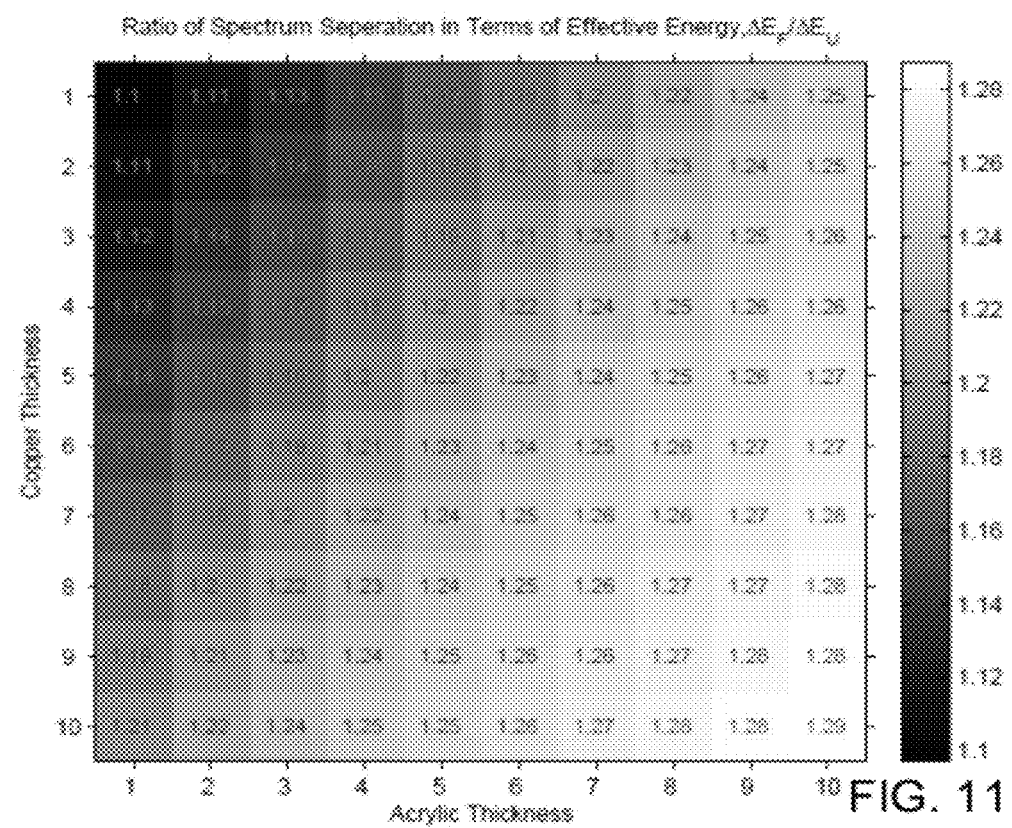

We used the simulated transmitted spectra to generate the energy separation map, as shown in FIGS. 11A-C, which shows that filtration increases the energy separation between the spectra by showing effective energy separation of the unfiltered low and high energy spectra in FIG. 11A, the filtered low and high energy spectra in FIG. 11B, and the ratio of the filtered to unfiltered energy separation in FIG. 11C. It does this primarily by increasing the effective energy of the high energy spectrum. The effective energies of the low and high spectra are displayed in each grid cell and the grayscale value indicates the separation. The ratio increases as the two materials became thicker, which may partially explain the variance reduction gradient in FIG. 11C. Notably, for thinner regions of the phantom, the low energy spectrum's effective energy increases due to the filtration, although the energy separation was still increased throughout the whole phantom. However, since the thicker region is more similar to the attenuation from human patients, this increase of effective energy at the thinner parts is not as much of a concern. In thicker regions, the low energy spectrum's effective energy decreases due to the filtration, which helps increase the separation of the spectra. Beam hardening plays an important role in increasing the effective energy separation beyond the K-edge effect of the filter, although as both spectra increase in effective energy, so too does their separation.

Our results demonstrate that the fixed $Gd_2O_2S$ filtration largely improves the precision of material decomposition so as to enhance the performance of rapid kVp-switching dual energy x-ray systems given the same exposure to the object. Alternative, we could reduce the radiation dose needed to achieve the same precision as without filtration. One downside of adding a filter, however, is the need to increase the tube current, which may require a higher power supply and exacerbate tube heating concerns. Nevertheless, this simple approach of adding a spectrum separation fixed filter can lead to significant dose reduction.

Unlike the clinical dual energy systems which operate at 80 and 140 kVp, our experiment used 70 and 125 kVp due to limitations of our benchtop system. Although the Gd filter was selected based on our initial simulations at 80/140 kVp, we still found it beneficial at 70/125 kVp.

An embodiment of the invention is based on initial simulation results of an optimal K-edge filter, conducted in a phantom experiment that demonstrated the potential of a fixed $Gd_2O_2S$ filtration to improve the material decomposition precision by as much as 40% for rapid kVp-switching dual energy systems for the same dose to the patient. Clinical applications will benefit from the improved dose efficiency provided by this readily available and inexpensive filter.

Embodiments

Figure 12:
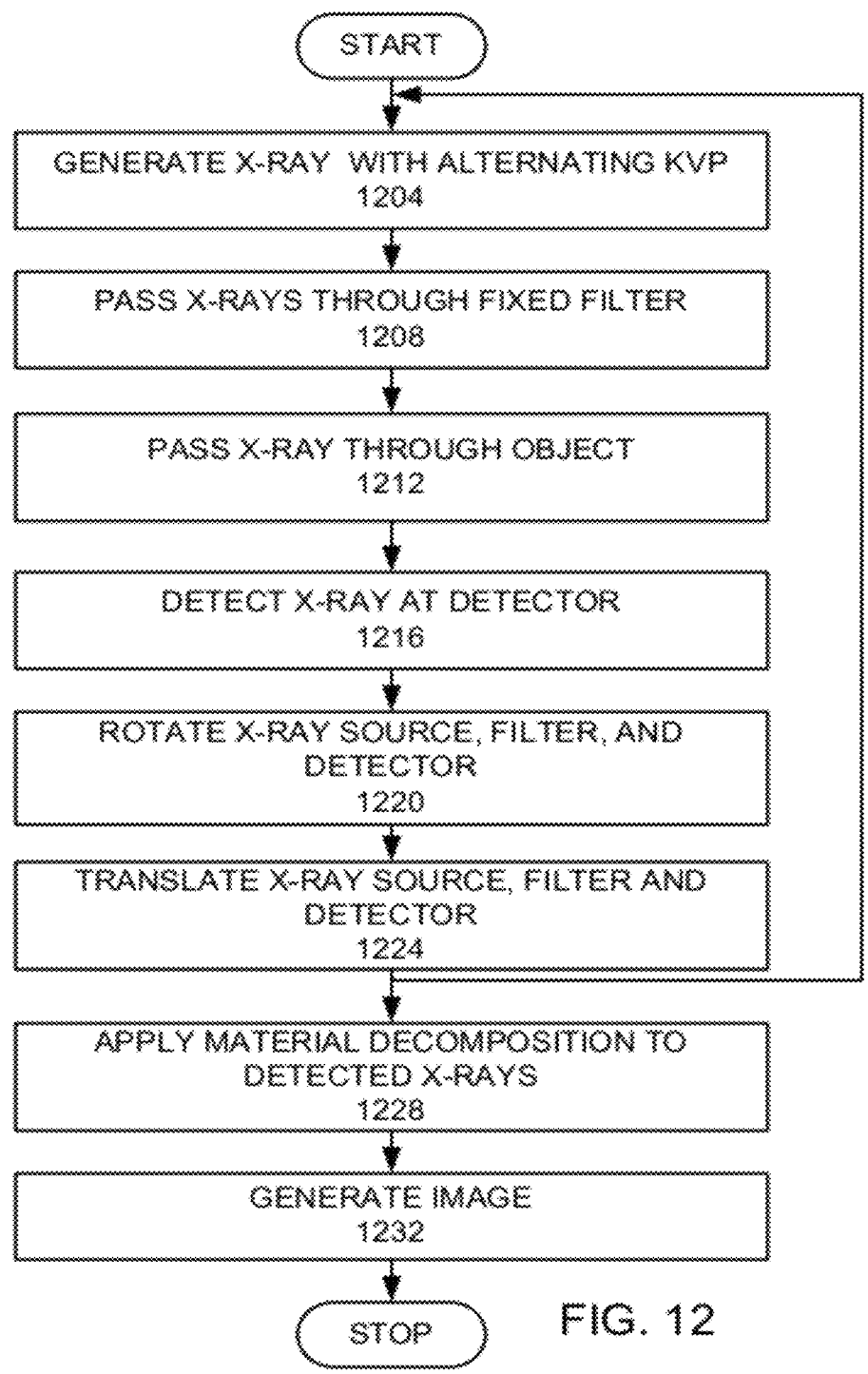
FIG. 12 is a high level flow chart of an embodiment of the invention.

To facilitate the understanding of the invention, FIG. 12 is a high level flow chart of an embodiment of the invention. An x-ray source provides at least two different alternating kVp x-rays with a first kVp potential and a second kVp potential (step 1204). The alternating x-rays are passed through a spectrum separation fixed filter (step 1208), where the spectrum separation fixed filter increases the detected spectrum separation between x-rays with the first kVp potential and x-rays with the second kVp potential. The x-rays pass through the object (step 1212). The x-rays are detected at the detector (step 1216). In a CT system embodiment the x-ray source, spectrum separation fixed filter, and detector are rotated around the object, where a center of rotation is along an axis of rotation (step 1220). To image a different section of the object the x-ray source, spectrum separation fixed filter, and detector are translated with respect to the object along the axis of rotation (step 1224). In one embodiment, this may be accomplished by moving the object on a support through an aperture. This process may be repeated one or more times. Material decomposition is applied to data from the detected x-rays (step 1228). At least one image is generated from the material decomposition of the data (step 1232). In a dual energy projection (non-CT) system, similar steps would be involved but may not include the relative motion and rotation of the imaging components with respect to the object being imaged.

Figure 13:
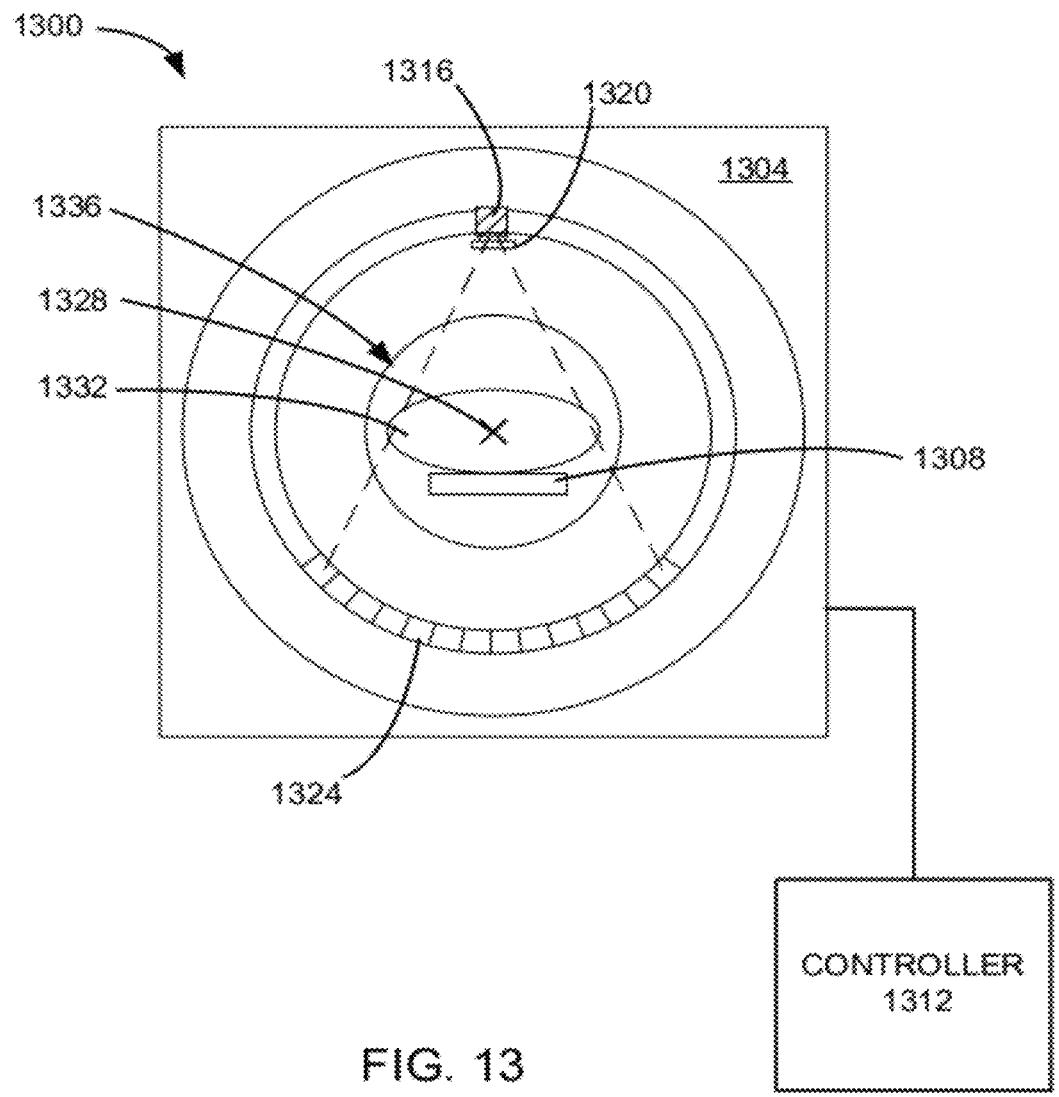
FIG. 13 is a schematic end view of a fast kVp x-ray switching CT system that may be used in an embodiment of the invention.
Figure 14:
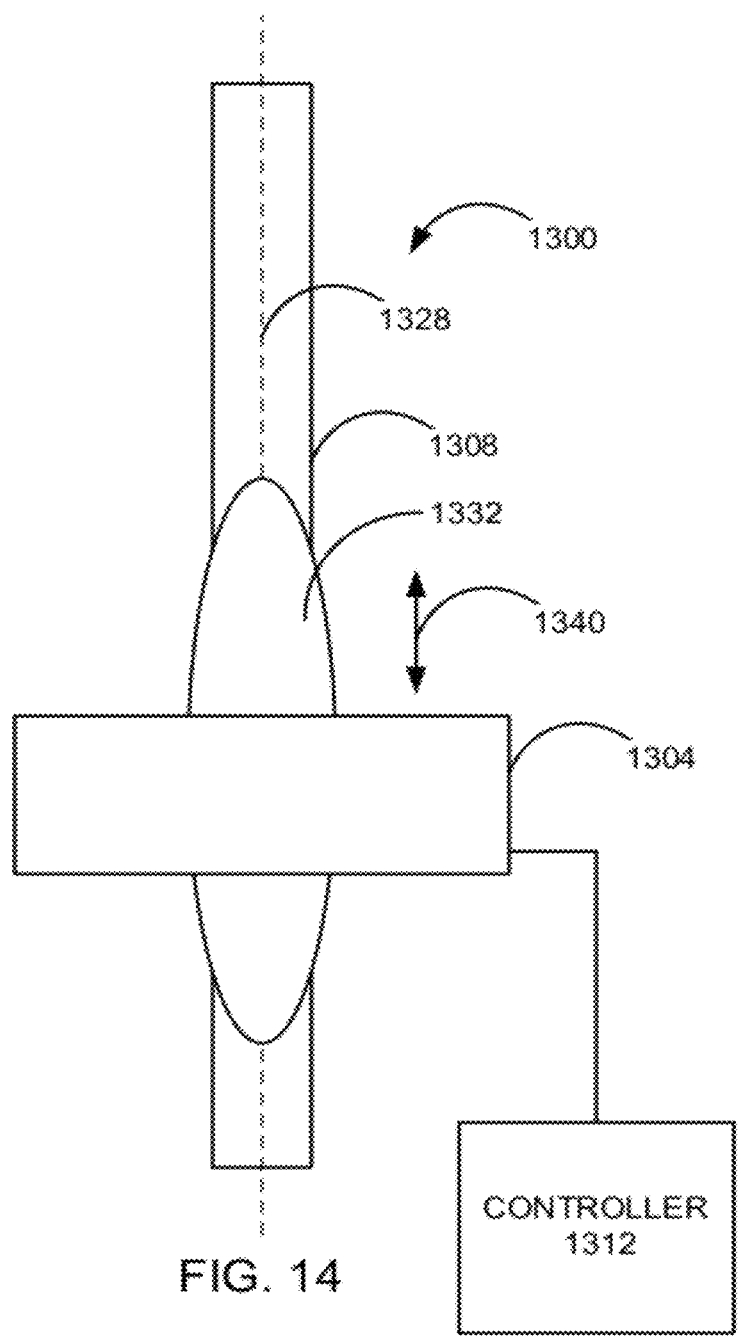
FIG. 14 is a top view of the fast kVp switching x-ray CT system.

In a more detailed example of an embodiment of the invention, FIG. 13 is a schematic end view of a multiple kVp x-ray CT system 1300 that may be used in an embodiment of the invention. The CT system comprises a gantry 1304, a support 1308, and a controller 1312. The gantry contains a multiple kVp x-ray source 1316, a spectrum separation fixed filter 1320, and an x-ray detector 1324. The gantry rotates the multiple kVp x-ray source 1316, spectrum separation fixed filter 1320, and x-ray detector 1324 around an axis of rotation 1328 that extends into the page. The support 1308 supports an object 1332 to be scanned. In this embodiment, the support 1308 translates the object with respect to the multiple kVp x-ray source 1316, spectrum separation fixed filter 1320, and x-ray detector 1324 along the axis of rotation 1328 through an aperture 1336 in the gantry 1304. FIG. 14 is a top view of the multiple kVp x-ray CT system 1300, showing the gantry 1304, the support 1308, the controller 1312, the object 1332, and the axis of rotation 1328. Arrow 1340 shows the direction of translation, which in this example is parallel to the axis of rotation 1328.

Figure 15:
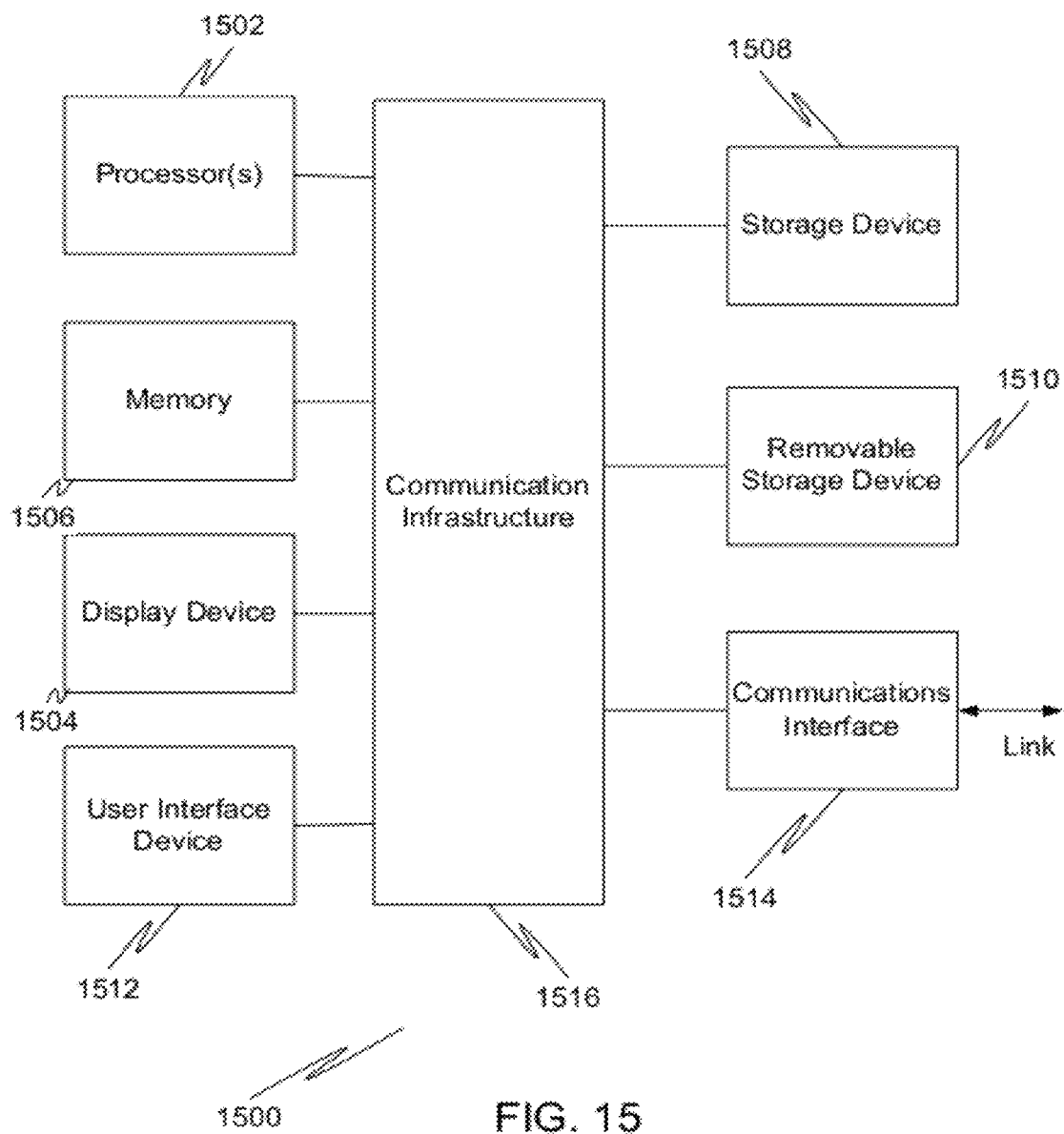
FIG. 15 is a high level block diagram showing a computer system, which is suitable for implementing a controller used in embodiments of the present invention.

FIG. 15 is a high level block diagram showing a computer system 1500, which is suitable for implementing a controller 1312 used in embodiments of the present invention. The computer system may have many physical forms ranging from an integrated circuit, a printed circuit board, and a small handheld device up to a huge super computer. The computer system 1500 includes one or more processors 1502, and further can include an electronic display device 1504 (for displaying graphics, text, and other data), a main memory 1506 (e.g., random access memory (RAM)), storage device 1508 (e.g., hard disk drive), removable storage device 1510 (e.g., optical disk drive), user interface devices 1512 (e.g., keyboards, touch screens, keypads, mice or other pointing devices, etc.), and a communication interface 1514 (e.g., wireless network interface). The communication interface 1514 allows software and data to be transferred between the computer system 1500 and external devices via a link. The system may also include a communications infrastructure 1516 (e.g., a communications bus, cross-over bar, or network) to which the aforementioned devices/modules are connected.

Information transferred via communications interface 1514 may be in the form of signals such as electronic, electromagnetic, optical, or other signals capable of being received by communications interface 1514, via a communication link that carries signals and may be implemented using wire or cable, fiber optics, a phone line, a cellular phone link, a radio frequency link, and/or other communication channels. With such a communications interface, it is contemplated that the one or more processors 1502 might receive information from a network, or might output information to the network in the course of performing the above-described method steps. Furthermore, method embodiments of the present invention may execute solely upon the processors or may execute over a network such as the Internet in conjunction with remote processors that share a portion of the processing.

The term "non-transient computer readable medium" is used generally to refer to media such as main memory, secondary memory, removable storage, and storage devices, such as hard disks, flash memory, disk drive memory, CD-ROM and other forms of persistent memory and shall not be construed to cover transitory subject matter, such as carrier waves or signals. Examples of computer code include machine code, such as produced by a compiler, and files containing higher level code that are executed by a computer using an interpreter. Computer readable media may also be computer code transmitted by a computer data signal embodied in a carrier wave and representing a sequence of instructions that are executable by a processor.

In this embodiment, the object 1332 is a person placed on the support 1308, which is a transport table. The transport table moves the person in a direction 1340 along the axis of rotation 1328 into the aperture 1336. When the part of the person that is to be imaged is within the aperture, the x-ray source 1316 provides at least two different alternating kVp x-rays with a first kVp potential and a second kVp potential (step 1204). In this example the x-ray source 1316 provides alternating x-rays of a kVp of 80 and a kVp of 140 that are alternated at a frequency of greater than 600 Hz. The x-rays pass through the spectrum separation fixed filter 1320 (step 1208). In this embodiment, the spectrum separation fixed filter 1320 is $Gd_2O_2S$, which is 83% Gd by mass and has a density of 7.44 g/cm³ and is 0.142 mm thick. The filter increases spectrum separation. This embodiment may also have other fixed filters such as beam hardening filters, and/or fixed bowtie filters as is known in the art. The x-rays then pass through the object 1332 (step 1212), which in this embodiment is part of a human body. The x-rays are then detected by the detector 1324 (step 1216).

The gantry 1304 rotates the x-ray source 1316, spectrum separation fixed filter 1320, and detector 1324 around the axis of rotation 1328 (step 1220). In this embodiment of the invention, a complete rotation is provided at a frequency of 1 Hz. The x-ray source 1316, spectrum separation fixed filter 1320 and detector 1324 are also translated with respect to the object 1332 (step 1224). In this embodiment, this is accomplished by moving the object 1332 through the aperture 1336. In this example, the object 1332 is moved at a speed of 4 cm/rev.

A material decomposition is applied to the detected x-rays (step 1228). One or more images are created from the data generated by the material decomposition (step 1232). In one embodiment, a plurality of cross-sectional images long an axis line are generated.

The presence of the spectrum separation fixed filter increases the spectral separation of the different kVp x-ray spectra. Such a separation allows for, decreasing noise, or decreasing x-ray exposure or ionized radiation. Preferably, the spectrum separation fixed filter comprises an atomic element with an atomic number between 60 and 72 inclusive. In a preferred embodiment, the spectrum separation fixed filter comprises Gadolinium. More preferably, the spectrum separation fixed filter comprises $Gd_2O_2S$.

Preferably, the spectrum separation fixed filter has a uniform thickness. Preferably, the spectrum separation fixed filter does not move or change with respect to the x-ray source during the scan, but instead moves simultaneously with the x-ray source during a scan. The filter may be switched between scans. A non-fixed filter that changes in synchrony with the alternating x-rays would be difficult to implement, given a fast kVp alternating frequency. It was found that a spectrum separation fixed filter of elements of with atomic numbers in a certain range allows for improved imaging with less noise and requiring a 40% less x-ray dose. The thickness of the spectrum separation fixed filter is a function of the density or purity of Gd. If it is pure Gd, the thickness of the spectrum separation fixed filter in one embodiment of the invention will be 119 microns, otherwise the thickness depends on the composition of the compound. Also this thickness is dependent on the limitation in an embodiment of the invention that the x-ray flux after the filtration is not cut more than half, since to compensate for the attenuated x-ray photons, the tube current limit must be pushed which is not favorable to the system. As shown in FIG. 2A, filter thickness is increased, to keep the total photons that will be incident to scanned object the same, the noise will decrease due to the further separated spectra. In embodiments of the invention, the lower kVp may be from 80 to 100 and the higher kVp may be from 120 to 160.

While this invention has been described in terms of several preferred embodiments, there are alterations, permutations, modifications and various substitute equivalents, which fall within the scope of this invention. It should also be noted that there are many alternative ways of implementing the methods and apparatuses of the present invention. It is therefore intended that the following appended claims be interpreted as including all such alterations, permutations, modifications, and various substitute equivalents as fall within the true spirit and scope of the present invention.

What is claimed is:

1. An apparatus for x-ray imaging of an object, comprising:
   an x-ray source for providing alternating x-ray spectrums placed on a first side of the object;
   a spectrum separation fixed filter between the x-ray source and the object, wherein the fixed filter does not move or change with respect to the x-ray source during a scan, wherein alternating x-ray spectrums pass through the spectrum separation fixed filter along a common path, so that the fixed filter increases spectrum separation of the alternating x-ray spectrums;
   an x-ray detector placed on a second side of the object opposite the x-ray source; and
   a controller for controlling the x-ray source and the x-ray detector.

2. The apparatus, as recited in claim 1, wherein the spectrum separation fixed filter comprises an atomic element with an atomic number between 60 and 72 inclusive.

3. The apparatus, as recited in claim 2, wherein the x-ray source provides kVp switching between at least two different kVp potentials.

4. The apparatus, as recited in claim 3, wherein the spectrum separation fixed filter comprises Gadolinium.

5. The apparatus, as recited in claim 4, wherein the spectrum separation fixed filter has a uniform thickness.

6. The apparatus, as recited in claim 1, wherein the apparatus for x-ray imaging is a multiple kVp switching x-ray computed tomography (CT) system.

7. The apparatus, as recited in claim 6, wherein the x-ray CT system further comprises:
   a gantry for supporting the x-ray source, spectrum separation fixed filter, and x-ray detector and for rotating the x-ray source, spectrum separation fixed filter, and x-ray detector around the object and an axis of rotation; and
   a translation system for moving the object relative to the gantry along the axis of rotation.

8. The apparatus, as recited in claim 3, wherein the spectrum separation fixed filter is a single filter element wherein x-rays from the at least two different kVp potentials pass through the single filter element.

9. The apparatus, as recited in claim 2, wherein the spectrum separation fixed filter provides a precision improvement of more than 40%.

10. The apparatus, as recited in claim 2, wherein the spectrum separation fixed filter comprises $Gd_2O_2S$.

11. A method for providing x-ray imaging of an object, comprising:
    a) providing from an x-ray source with at least two different alternating kVp x-rays with a first kVp potential and a second kVp potential;
    b) passing the alternating kVp x-rays through a spectrum separation fixed filter, wherein the alternating kVp x-rays pass through the spectrum separation fixed filter along a common path, so that the spectrum separation fixed filter increases spectrum separation between x-rays with the first kVp potential and x-rays with the second kVp potential, wherein the fixed filter does not move or change with respect to the x-ray source during a scan;
    c) passing the kVp x-rays through the object;
    d) detecting at a detector the x-rays that pass through the object at the first kVp potential and the second kVp potential;
    e) applying material decomposition to detected x-rays; and
    f) using the material decomposition to generate an image.

12. The method, as recited in claim 11, wherein the single spectrum separation fixed filter comprises an atomic element with an atomic number between 60 and 72 inclusive.

13. The method, as recited in claim 12, wherein the spectrum separation fixed filter comprises Gadolinium.

14. The method, as recited in claim 13, wherein the spectrum separation fixed filter has a uniform thickness.

15. The method, as recited in claim 14, further comprising:
    rotating the x-ray source, spectrum separation fixed filter, and the detector around an axis of rotation; and
    translating the object relative to the x-ray source, spectrum separation fixed filter, and detector along the axis of rotation.

16. The method, as recited in claim 15, wherein the using the material decomposition to generate the image uses computed tomography.

17. The method, as recited in claim 16, wherein the spectrum separation fixed filter comprises $Gd_2O_2S$.

18. The method, as recited in claim 12, wherein the spectrum separation fixed filter provides a precision improvement of more than 40%.

19. The method, as recited in claim 12, wherein the spectrum separation fixed filter comprises $Gd_2O_2S$.

* * * * *